United States Patent [19]
Or et al.

[11] Patent Number: 5,922,683
[45] Date of Patent: Jul. 13, 1999

[54] MULTICYCLIC ERYTHROMYCIN DERIVATIVES

[75] Inventors: Yat Sun Or, Libertyville, Ill.; George Griesgraber, Eagan, Minn.; Daniel T. Chu, Santa Clara, Calif.

[73] Assignee: Abbott Laboratories, Abbott Park, Ill.

[21] Appl. No.: 09/087,035

[22] Filed: May 29, 1998

Related U.S. Application Data

[60] Provisional application No. 60/050,928, May 29, 1997.
[51] Int. Cl.$^6$ ............................ A61K 31/70; C07H 17/08
[52] U.S. Cl. ................................ 514/29; 536/7.2; 536/7.4
[58] Field of Search ............................... 514/29; 536/7.2, 536/7.4

[56] References Cited

U.S. PATENT DOCUMENTS

| | | | |
|---|---|---|---|
| 5,403,923 | 4/1995 | Kashimura et al. | 563/7.4 |
| 5,527,780 | 6/1996 | Agouridas et al. | 514/29 |
| 5,543,400 | 8/1996 | Agouridas et al. | 514/29 |
| 5,561,118 | 10/1996 | Agouridas et al. | 514/29 |

FOREIGN PATENT DOCUMENTS

| | | |
|---|---|---|
| 0638585 | 2/1995 | European Pat. Off. . |
| 0676409 | 10/1995 | European Pat. Off. . |
| 9321200 | 10/1993 | WIPO . |
| WO9717356 | 5/1997 | WIPO . |
| 9822488 | 5/1998 | WIPO . |

*Primary Examiner*—Marian C. Knode
*Assistant Examiner*—L. Eric Crane
*Attorney, Agent, or Firm*—Mona Anand

[57] ABSTRACT

Novel multicyclic erythromycin compounds and pharmaceutically acceptable salts and esters thereof having antibacterial activity having a formula

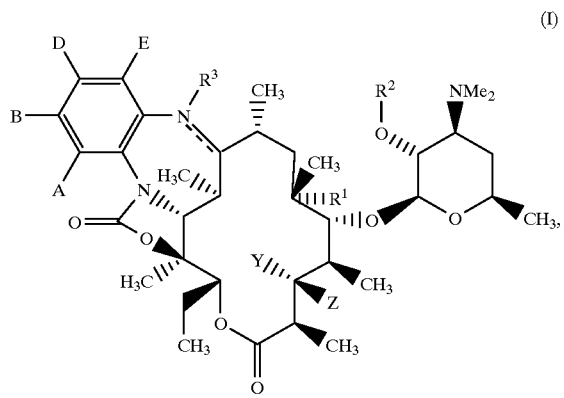

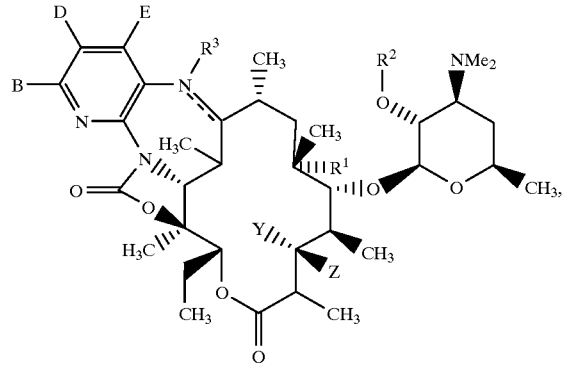

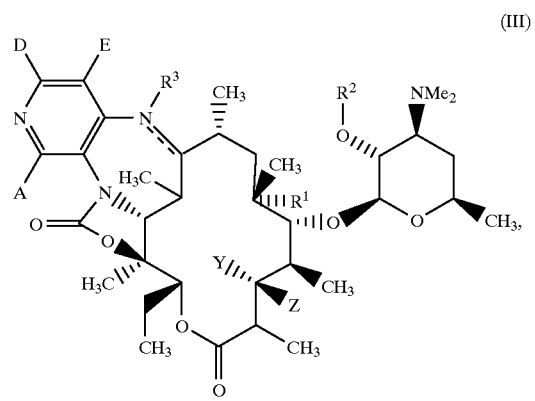

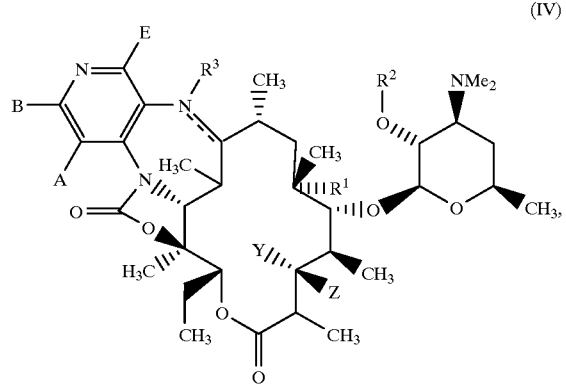

-continued

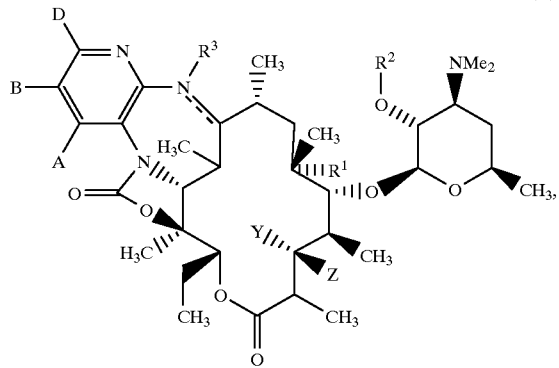
(V)

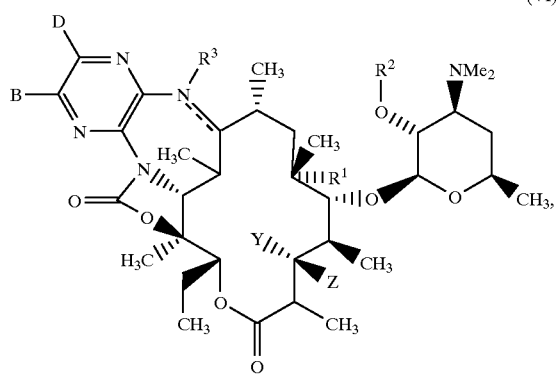
(VI)

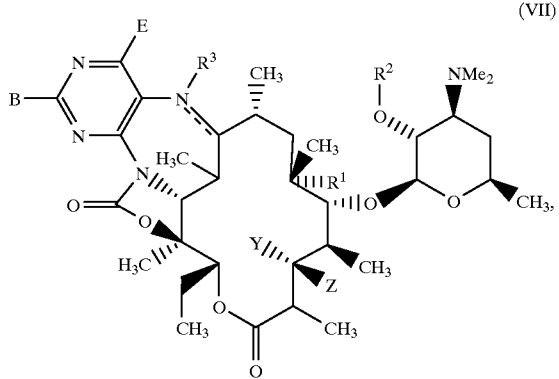
(VII)

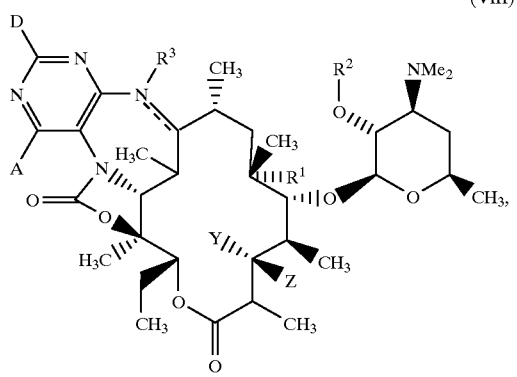
(VIII)

-continued

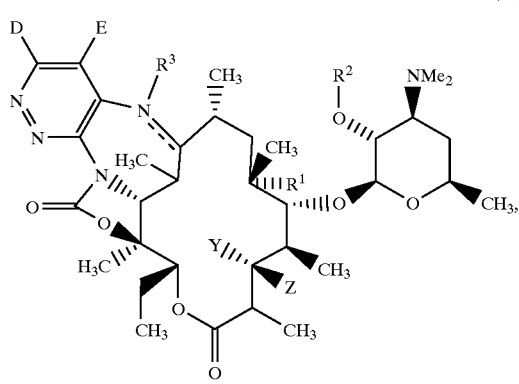
(IX)

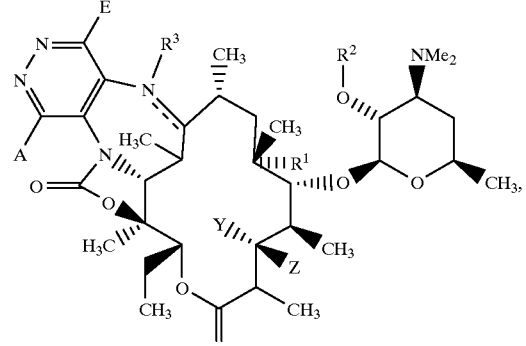
(X)

or

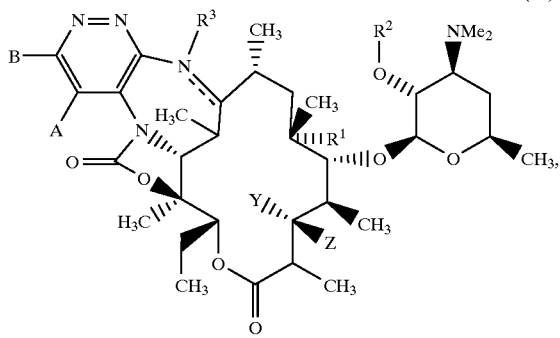
(XI)

pharmaceutical compositions comprising a therapeutically effective amount of a compound of the invention in combination with a pharmaceutically acceptable carrier, as well as a method for treating bacterial infections by administering to a mammal a pharmaceutical composition containing a therapeutically-effective amount of a compound of formula (I).

29 Claims, No Drawings

MULTICYCLIC ERYTHROMYCIN DERIVATIVES

This application claims the benefit of U.S. Provisional Application for Ser. No. 60/050,928, filed May 29, 1997.

TECHNICAL FIELD

The present invention relates to semisynthetic macrolides having antibacterial activity and useful in the treatment and prevention of bacterial infections. More particularly, the invention relates to multicyclic erythromycin derivatives, compositions containing such compounds and methods for using the same, as well as processes for making such compounds.

BACKGROUND OF THE INVENTION

Erythromycins A through D, represented by formula (E),

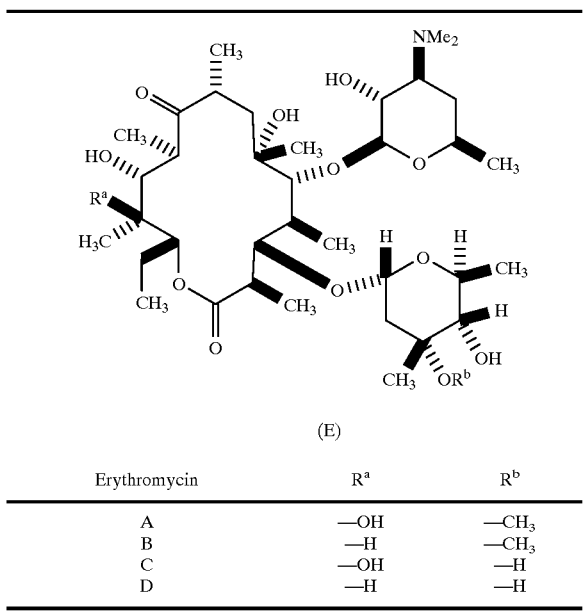

(E)

| Erythromycin | $R^a$ | $R^b$ |
|---|---|---|
| A | —OH | —$CH_3$ |
| B | —H | —$CH_3$ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

We have discovered that multicyclic erythromycin derivatives containing one or more fused aryl or heteroaryl ring possess significant activity against selected microorganisms.

Other variously modified erythromycin compounds are known, but none possess the fused aryl or heteroaryl ring moieties of the present invention (see, for example, Agouridas et al., European application EP676409, published Oct. 11, 1995; Agouridas et al., U.S. Pat. No. 5,527,780, issued Jun. 18, 1996; Agouridas et al., U.S. Pat. No. 5,543,400, issued Aug. 6, 1996; Kashimura et al., U.S. Pat. No. 5,403,923, issued Apr. 4, 1995, and Asaka et al., PCT application WO 93/21200, published Oct. 28, 1993). Also, Agouridas et al., U.S. Pat. No. 5,561,118, issued Oct. 1, 1996, describe erythromycin derivatives with the 3-cladinose moiety removed.

SUMMARY OF THE INVENTION

The present invention provides a novel class of multicyclic erythromycin derivatives that possess antibacterial activity.

In one aspect of the present invention are compounds, or pharmaceutically acceptable salts and esters thereof, having a formula selected from the group consisting of

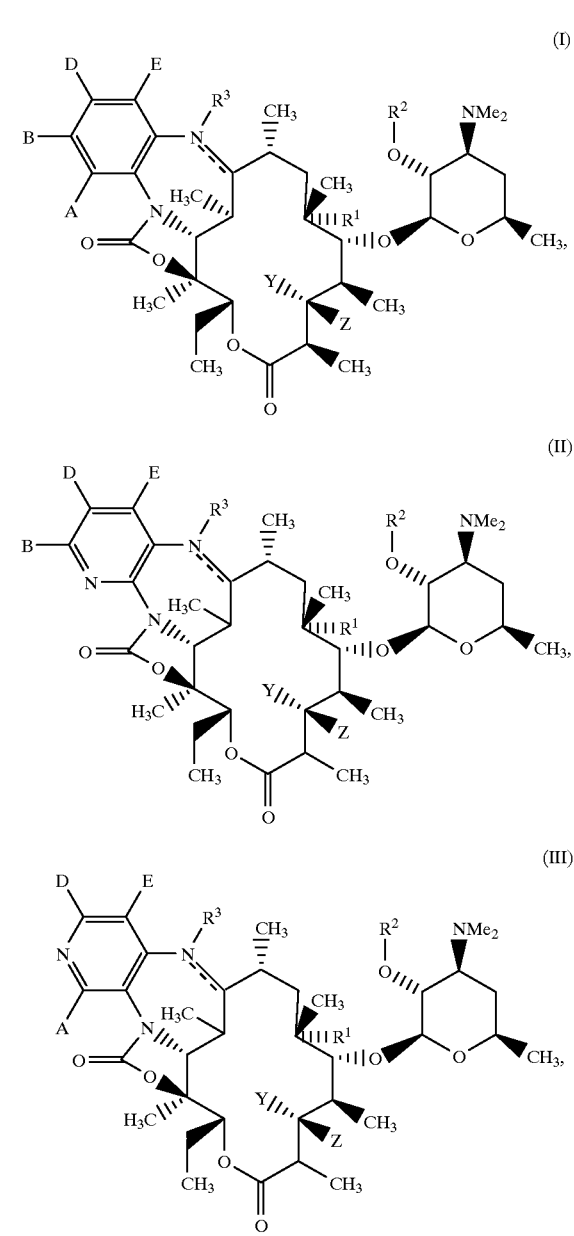

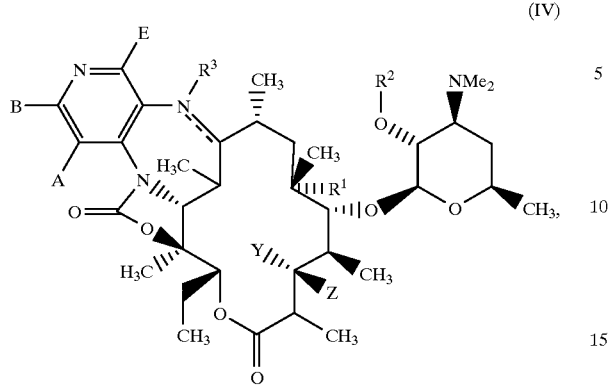
(IV)
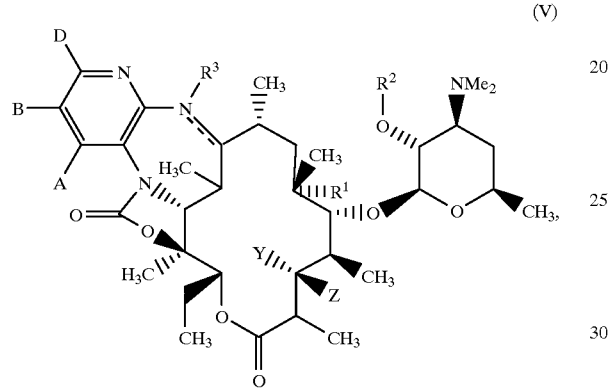
(V)
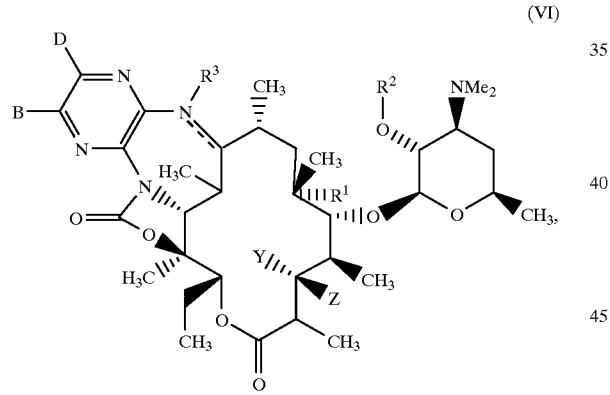
(VI)
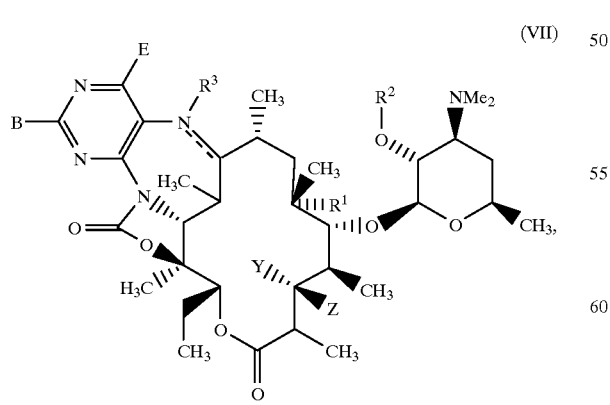
(VII)
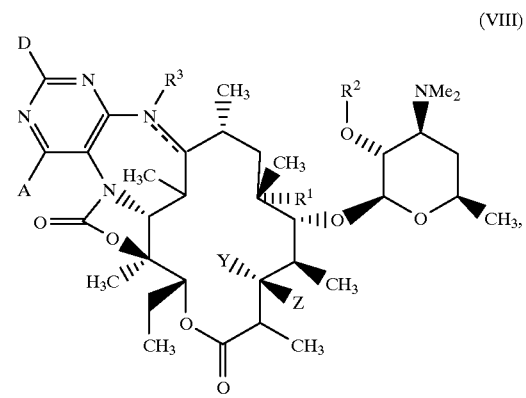
(VIII)
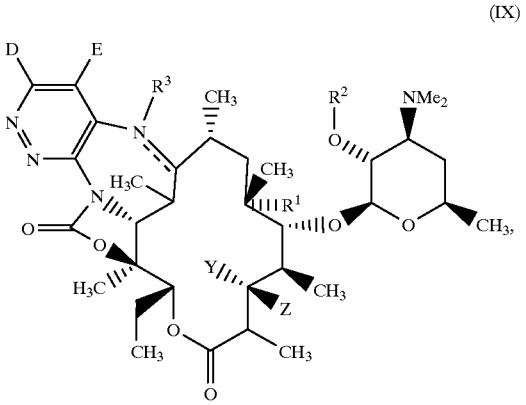
(IX)
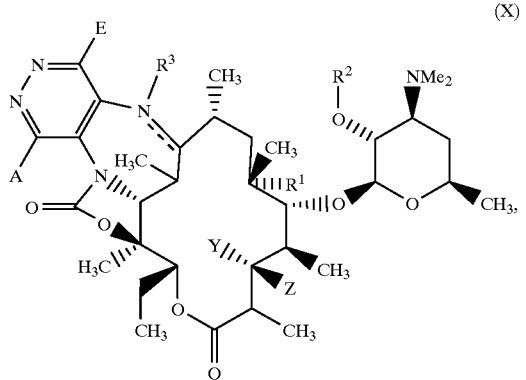
(X)
and
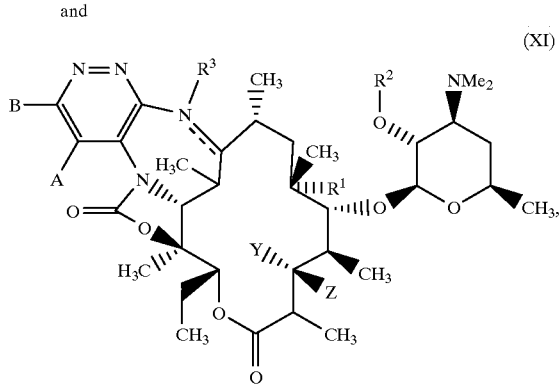
(XI)

wherein each of A, B, D and E is independently a group having the formula —$(CH_2)_m$—M—$(CH_2)_n$—X, wherein m is 0, 1, 2 or 3;

n is 0, 1, 2 or 3;

M is absent or is selected from the group consisting of:
(i) —O—;
(ii) —NH—;
(iii) —$NR^4$—, wherein $R^4$ is $C_1$–$C_6$-alkyl optionally substituted with halogen, aryl or heteroaryl;
(iv) —$S(O)_q$—, wherein q is 0, 1 or 2;
(V) —C(O)—;
(vi) —C(O)—NH—;
(vii) —NH—C(O)—;
(viii) —C(O)—O—
(ix) —O—C(O)—;
(x) —CH=CH—;
(xi) —C≡C—; and X is selected from the group consisting of:
(i) H;
(ii) CN;
(iii) halogen;
(iv) $NO_2$;
(v) aryl;
(vi) substituted-aryl;
(vii) heteroaryl;
(viii) substituted-heteroaryl;
(ix) heterocycloalkyl; and
(x) $C_3$–$C_7$-cycloalkyl;
(xi) $C_1$–$C_6$-alkyl;
(xii) $C_1$–$C_6$-acyl; or one pair of A, B, D and E, selected from the group consisting of A&B, B&D, and D&E, may, when such combinations are possible, additionally combine with the atoms to which they are attached to form a ring selected from the group consisting of benzene, pyridine, pyridazine, pyrimidine, pyrazine, pryazole, imidazole, triazole, pyrrole, furan, thiophene, oxazole, 1,3-dioxocyclopent-2-ene and 1,4-dioxocyclohex-2-ene;

$R^1$ is selected from the group consisting of:
(a) hydrogen;
(b) hydroxy;
(c) a protected hydroxy group;
(d) methoxy;
(e) O—R, wherein R is selected from the group consisting of
(1) methyl substituted with a moiety selected from the group consisting of
(a) CN,
(b) F,
(c) —$CO_2R^5$ wherein $R^5$ is $C_1$–$C_3$-alkyl or aryl substituted $C_1$–$C_3$-alkyl, or heteroaryl substituted $C_1$–$C_3$-alkyl,
(d) $S(O)_nR^5$ where n is 0, 1 or 2 and $R^5$ is as defined above,
(e) $C(O)NHR^5$ where $R^5$ is as defined above,
(f) $C(O)NR^6R^7$ wherein $R^6$ and $R^7$ are independently selected from hydrogen and $C_1$–$C_3$-alkyl,
(g) aryl,
(h) substituted aryl,
(i) heteroaryl, and
(j) substituted heteroaryl,
(2) $C_2$–$C_{10}$-alkyl,
(3) $C_2$–$C_{10}$-alkyl substituted with one or more substituents selected from the group consisting of (a) halogen,
(b) hydroxy,
(c) $C_1$–$C_3$-alkoxy,
(d) $C_1$–$C_3$-alkoxy-$C_1$–$C_3$-alkoxy,
(e) oxo,
(f) —$N_3$,
(g) —CHO,
(h) O—$SO_2$-(substituted $C_1$–$C_6$-alkyl),
(i) —$NR^8R^9$ wherein $R^8$ and $R^9$ are selected from the group consisting of
(i) hydrogen,
(ii) $C_1$–$C_{12}$-alkyl,
(iii) substituted $C_1$–$C_{12}$-alkyl,
(iv) $C_1$–$C_{12}$-alkenyl,
(v) substituted $C_1$–$C_{12}$-alkenyl,
(vi) $C_1$–$C_{12}$-alkynyl,
(vii) substituted $C_1$–$C_{12}$-alkynyl,
(viii) aryl,
(ix) $C_3$–$C_8$-cycloalkyl,
(x) substituted $C_3$–$C_8$-cycloalkyl,
(xi) substituted aryl,
(xii) heterocycloalkyl,
(xiii) substituted heterocycloalkyl,
(xiv) $C_1$–$C_{12}$-alkyl substituted with aryl,
(xv) $C_1$–$C_{12}$-alkyl substituted with substituted aryl,
(xvi) $C_1$–$C_{12}$-alkyl substituted with heterocycloalkyl,
(xvii) $C_1$–$C_{12}$-alkyl substituted with substituted heterocycloalkyl,
(xviii) $C_1$–$C_{12}$-alkyl substituted with $C_3$–$C_8$-cycloalkyl,
(xix) $C_1$–$C_{12}$-alkyl substituted with substituted $C_3$–$C_8$-cycloalkyl,
(xx) heteroaryl,
(xxi) substituted heteroaryl,
(xxii) $C_1$–$C_{12}$-alkyl substituted with heteroaryl, and
(xxiii) $C_1$–$C_{12}$-alkyl substituted with substituted heteroaryl,
or $R^8$ and $R^9$ are taken together with the atom to which they are attached form a 3–10 membered heterocycloalkyl ring which may be substituted with one or more substituents independently selected from the group consisting of:
(i) halogen,
(ii) hydroxy,
(iii) $C_1$–$C_3$-alkoxy,
(iv) $C_1$–$C_3$-alkoxy-$C_1$–$C_3$-alkoxy,
(v) oxo,
(vi) $C_1$–$C_3$-alkyl,
(vii) halo-$C_1$–$C_3$-alkyl, and
(vii) $C_1$–$C_3$-alkoxy-$C_1$–$C_3$-alkyl,
(j) —$CO_2R^5$ wherein $R^5$ is as defined above,
(k) —$C(O)NR^6R^7$ wherein $R^6$ and $R^7$ are as defined above,
(l) =N—O—$R^5$ wherein $R^5$ is as previously defined,
(m) —C≡N,
(n) O—$S(O)_nR^5$ wherein n is 0, 1 or 2 and $R^5$ is as defined above,
(o) aryl,
(p) substituted aryl,
(q) heteroaryl,
(r) substituted heteroaryl,
(s) $C_3$–$C_8$-cycloalkyl,
(t) substituted $C_3$–$C_8$-cycloalkyl, (u) $C_1$–$C_{12}$-alkyl substituted with heteroaryl,
(v) heterocycloalkyl,
(w) substituted heterocycloalkyl,
(x) NHC(O)$R^5$ where $R^5$ is as previously defined,
(y) NHC(O)NR$^6$R$^7$ wherein $R^6$ and $R^7$ are as previously defined,
(z) =N—NR$^8$R$^9$ wherein $R^8$ and $R^9$ are as previously defined,
(aa) =N—R$^{11}$ wherein $R^{11}$ is selected from the group consisting of:
  (i) $C_1$–$C_6$-alkyl, optionally substituted with a substituent selected from the group consisting of
    (aa) aryl,
    (bb) substituted-aryl,
    (cc) heteroaryl, and
    (dd) substituted-heteroaryl,
  (ii) aryl,
  (iii) substituted-aryl,
  (iv) heteroaryl,
  (v) substituted-heteroaryl, and
  (vi) heterocycloalkyl,
(bb) =N—NHC(O)$R^5$ wherein $R^5$ is as previously defined, and
(cc) =N—NHC(O)NR$^6$R$^7$ wherein $R^6$ and $R^7$ are as previously defined;
(4) $C_3$-alkenyl substituted with a moiety selected from the group consisting of
(a) halogen,
(b) —CHO,
(c) —CO$_2$R$^5$ where $R^5$ is as defined above,
(d) —C(O)—R$^{11}$ where $R^{11}$ is as defined above,
(e) —C(O)NR$^6$R$^7$ wherein $R^6$ and $R^7$ are as previously defined,
(f) —C≡N,
(g) aryl,
(h) substituted aryl,
(i) heteroaryl,
(j) substituted heteroaryl,
(k) $C_3$–$C_7$-cycloalkyl, and
(l) $C_1$–$C_{12}$-alkyl substituted with heteroaryl,
(5) $C_4$–$C_{10}$-alkenyl;
(6) $C_4$–$C_{10}$-alkenyl substituted with one or more substituents selected from the group consisting of
(a) halogen,
(b) $C_1$–$C_3$-alkoxy,
(c) oxo,
(d) —CHO,
(e) —CO$_2$R$^5$ where $R^5$ is as defined above,
(f) —C(O)NR$^6$R$^7$ wherein $R^6$ and $R^7$ are as previously defined,
(g) —NR$^8$R$^9$ wherein $R^8$ and $R^9$ are as previously defined,
(h) =N—O—R$^5$ where $R^5$ is as previously defined,
(i) —C≡N,
(j) O—S(O)$_n$R$^5$ where n is 0, 1 or 2 and $R^5$ is as previously defined,
(k) aryl,
(l) substituted aryl,
(m) heteroaryl,
(n) substituted heteroaryl,
(o) $C_3$–$C_7$-cycloalkyl,
(p) $C_1$–$C_{12}$-alkyl substituted with heteroaryl,
(q) NHC(O)$R^5$ where $R^5$ is as previously defined,
(r) NHC(O)NR$^6$R$^7$ wherein $R^6$ and $R^7$ are as previously defined,
(s) =N—NR$^8$R$^9$ wherein $R^8$ and $R^9$ are as previously defined,
(t) =N—R$^{11}$ wherein $R^{11}$ is as previously defined,
(u) =N—NHC(O)$R^5$ where $R^5$ is as previously defined, and (v) =N—NHC(O)NR$^6$R$^7$ wherein $R^6$ and $R^7$ are as previously defined;
(7) $C_3$–$C_{10}$-alkynyl; and
(8) $C_3$–$C_{10}$-alkynyl substituted with one or more substituents selected from the group consisting of
  (a) trialkylsilyl,
  (b) aryl,
  (c) substituted aryl,
  (d) heteroaryl, and
  (e) substituted heteroaryl;
$R^2$ is hydrogen or a hydroxy protecting group;
the dashed line represents an optional double bond;
$R^3$ is absent or oxygen when the optional double bond is present;
$R^3$ is hydrogen, hydroxy, $C_1$–$C_6$-acyl or $C_1$–$C_6$-alkyl optionally substituted with halogen, aryl or heteroaryl, when the optional double bond is absent; and
Y and Z are both hydrogen, or one of Y and Z is hydrogen and the other is selected from the group consisting of hydroxy, protected hydroxy, and cladinose, or Y and Z are taken together with the atom to which they are attached to form an oxo group.

In another aspect of the present invention are disclosed pharmaceutical compositions for treating bacterial infections comprising a therapeutically effective amount of a compound of the invention in combination with a pharmaceutically acceptable carrier. Suitable carriers and methods of formulation are also disclosed.

Still another aspect of this invention is a method for treating bacterial infections comprising administering to a mammal in need of such treatment a pharmaceutical composition containing a therapeutically-effective amount of a compound of the invention.

In a further aspect of the invention is provided a process for the preparation of multicyclic macrolide compounds of Formula (I)–(XI) above.

DETAILED DESCRIPTION OF THE INVENTION

In a first embodiment of the invention is a compound having the formula (I) as described above. One preferred embodiment is a compound of formula (I) wherein Y and Z are both hydrogen. In another preferred embodiment is a compound of formula (I) wherein one of Y and Z is hydrogen and the other is selected from the group consisting of hydroxy, protected hydroxy, and cladinose. In still another preferred embodiment is a compound of formula (I) wherein Y and Z are taken together with the atom to which they are attached to form an oxo group.

In a second embodiment of the invention is a compound having the formula (II) as described above. One preferred embodiment is a compound of formula (II) wherein Y and Z are both hydrogen. In another preferred embodiment is a compound of formula (II) wherein one of Y and Z is hydrogen and the other is selected from the group consisting of hydroxy, protected hydroxy, and cladinose. In still another preferred embodiment is a compound of formula (II) wherein Y and Z are taken together with the atom to which they are attached to form an oxo group.

In a third embodiment of the invention is a compound having the formula (III) as described above. One preferred embodiment is a compound of formula (III) wherein Y and Z are both hydrogen. In another preferred embodiment is a compound of formula (III) wherein one of Y and Z is hydrogen and the other is selected from the group consisting of hydroxy, protected hydroxy, and cladinose. In still another preferred embodiment is a compound of formula (III) wherein Y and Z are taken together with the atom to which they are attached to form an oxo group.

In a fourth embodiment of the invention is a compound having the formula (IV) as described above. One preferred embodiment is a compound of formula (IV) wherein Y and Z are both hydrogen. In another preferred embodiment is a compound of formula (IV) wherein one of Y and Z is hydrogen and the other is selected from the group consisting of hydroxy, protected hydroxy, and cladinose. In still another preferred embodiment is a compound of formula (IV) wherein Y and Z are taken together with the atom to which they are attached to form an oxo group.

In a fifth embodiment of the invention is a compound having the formula (V) as described above. One preferred embodiment is a compound of formula (V) wherein Y and Z are both hydrogen. In another preferred embodiment is a compound of formula (V) wherein one of Y and Z is hydrogen and the other is selected from the group consisting of hydroxy, protected hydroxy, and cladinose. In still another preferred embodiment is a compound of formula (V) wherein Y and Z are taken together with the atom to which they are attached to form an oxo group.

In a sixth embodiment of the invention is a compound having the formula (VI) as described above. One preferred embodiment is a compound of formula (VI) wherein Y and Z are both hydrogen. In another preferred embodiment is a compound of formula (VI) wherein one of Y and Z is hydrogen and the other is selected from the group consisting of hydroxy, protected hydroxy, and cladinose. In still another preferred embodiment is a compound of formula (VI) wherein Y and Z are taken together with the atom to which they are attached to form an oxo group.

In a seventh embodiment of the invention is a compound having the formula (VII) as described above. One preferred embodiment is a compound of formula (VII) wherein Y and Z are both hydrogen. In another preferred embodiment is a compound of formula (VII) wherein one of Y and Z is hydrogen and the other is selected from the group consisting of hydroxy, protected hydroxy, and cladinose. In still another preferred embodiment is a compound of formula (VII) wherein Y and Z are taken together with the atom to which they are attached to form an oxo group.

In an eighth embodiment of the invention is a compound having the formula (VIII) as described above. One preferred embodiment is a compound of formula (VIII) wherein Y and Z are both hydrogen. In another preferred embodiment is a compound of formula (VIII) wherein one of Y and Z is hydrogen and the other is selected from the group consisting of hydroxy, protected hydroxy, and cladinose. In still another preferred embodiment is a compound of formula (VIII) wherein Y and Z are taken together with the atom to which they are attached to form an oxo group.

In a ninth embodiment of the invention is a compound having the formula (IX) as described above. One preferred embodiment is a compound of formula (IX) wherein Y and Z are both hydrogen. In another preferred embodiment is a compound of formula (IX) wherein one of Y and Z is hydrogen and the other is selected from the group consisting of hydroxy, protected hydroxy, and cladinose. In still another preferred embodiment is a compound of formula (IX) wherein Y and Z are taken together with the atom to which they are attached to form an oxo group.

In a tenth embodiment of the invention is a compound having the formula (X) as described above. One preferred embodiment is a compound of formula (X) wherein Y and Z are both hydrogen. In another preferred embodiment is a compound of formula (X) wherein one of Y and Z is hydrogen and the other is selected from the group consisting of hydroxy, protected hydroxy, and cladinose. In still another preferred embodiment is a compound of formula (X) wherein Y and Z are taken together with the atom to which they are attached to form an oxo group.

In an eleventh embodiment of the invention is a compound having the formula (XI) as described above. One preferred embodiment is a compound of formula (XI) wherein Y and Z are both hydrogen. In another preferred embodiment is a compound of formula (XI) wherein one of Y and Z is hydrogen and the other is selected from the group consisting of hydroxy, protected hydroxy, and cladinose. In still another preferred embodiment is a compound of formula (XI) wherein Y and Z are taken together with the atom to which they are attached to form an oxo group.

Representative compounds of the invention are those selected from the group consisting of:

Compound of Formula (I): $R^1$ is methoxy; $R^2$ is H, $R^3$ is absent, the double bond is present, A, B, D and E are H, and Y and Z taken together with the atom to which they are attached form an oxo group;

Compound of Formula (I): $R^1$ is methoxy; $R^2$ is H, $R^3$ is H, the double bond is absent, A, B, D and E are H, and Y and Z taken together with the atom to which they are attached form an oxo group;

Compound of Formula (I): $R^1$ is methoxy; $R^2$ is H, $R^3$ is absent, the double bond is present, A, B, and E are H, D is methyl, and Y and Z taken together with the atom to which they are attached form an oxo group;

Compound of Formula (I): $R^1$ is methoxy; $R^2$ is H, $R^3$ is absent, the double bond is present, A, B, and E are H, D is methoxy, and Y and Z taken together with the atom to which they are attached form an oxo group;

Compound of Formula (I): $R^1$ is methoxy; $R^2$ is H, $R^3$ is absent, the double bond is present, A, B, and E are H, D is cyano, and Y and Z taken together with the atom to which they are attached form an oxo group;

Compound of Formula (II): $R^1$ is methoxy; $R^2$ is H, $R^3$ is absent, the double bond is present, B, D, and E are H, and Y and Z taken together with the atom to which they are attached form an oxo group;

Compound of Formula (I): $R^1$ is allyloxy; $R^2$ is H, $R^3$ is absent, the double bond is present, A, B, D and E are H, and Y and Z taken together with the atom to which they are attached form an oxo group;

Compound of Formula (I): $R^1$ 3-(3-quinolinyl)allyloxy; $R^2$ is H, $R^3$ is absent, the double bond is present, A, B, D and E are H, and Y and Z taken together with the atom to which they are attached form an oxo group;

Compound of Formula (I): $R^1$ is allyloxy; $R^2$ is H, $R^3$ is absent, the double bond is present, A, B, D and E are H, Y is H, and Z is cladinose;

Compound of Formula (I): $R^1$ is 3-(3-quinolinyl)allyloxy; $R^2$ is H, $R^3$ is absent, the double bond is present, A, B, D and E are H, Y is H, and Z is cladinose;

Compound of Formula (III): $R^1$ is methoxy; $R^2$ is H, $R^3$ is absent, the double bond is present, A, D, and E are H, and Y and Z taken together with the atom to which they are attached form an oxo group;

Compound of Formula (IV): $R^1$ is methoxy; $R^2$ is H, $R^3$ is absent, the double bond is present, A, B, and E are H, and Y and Z taken together with the atom to which they are attached form an oxo group;

Compound of Formula (V): $R^1$ is methoxy; $R^2$ is H, $R^3$ is absent, the double bond is present, A. B, and D are H, and Y and Z taken together with the atom to which they are attached form an oxo group;

Compound of Formula (VI): $R^1$ is methoxy; $R^2$ is H, $R^3$ is absent, the double bond is present, B and D are H, and Y and Z taken together with the atom to which they are attached form an oxo group;

Compound of Formula (VII): $R^1$ is methoxy; $R^2$ is H, $R^3$ is absent, the double bond is present, B and E are H, and Y and Z taken together with the atom to which they are attached form an oxo group;

Compound of Formula (VIII): $R^1$ is methoxy; $R^2$ is H, $R^3$ is absent, the double bond is present, A and D are H, and Y and Z taken together with the atom to which they are attached form an oxo group;

Compound of Formula (IX): $R^1$ is methoxy; $R^2$ is H, $R^3$ is absent, the double bond is present, D and E are H, and Y and Z taken together with the atom to which they are attached form an oxo group;

Compound of Formula (X): $R^1$ is methoxy; $R^2$ is H, $R^3$ is absent, the double bond is present, A and E are H, and Y and Z taken together with the atom to which they are attached form an oxo group; and Compound of Formula (XI): $R^1$ is methoxy; $R^2$ is H, $R^3$ is absent, the double bond is present, A and B are H, and Y and Z taken together with the atom to which they are attached form an oxo group.

One aspect of the invention is a process for preparing a compound selected from the group consisting of compounds of formula (I) through (XI) as previously defined comprising (a) treating in an aprotic solvent in the presence of a base a compound having the formula

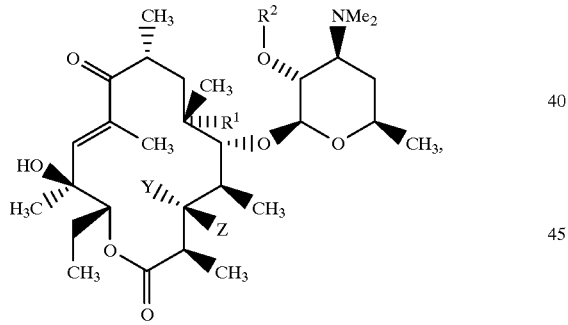

wherein
$R^2$ is hydrogen or a hydroxy protecting group; and
$R^1$, Y and Z are as previously defined;
with a reagent selected from the group consisting of
(1) an isocyanate compound having the formula Nitroaryl—N=C=O, wherein the Nitroaryl moiety is selected from the group consisting of

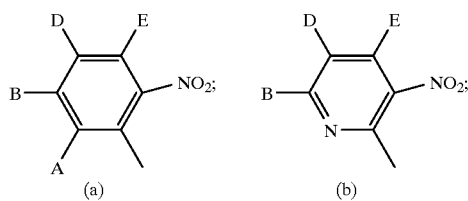

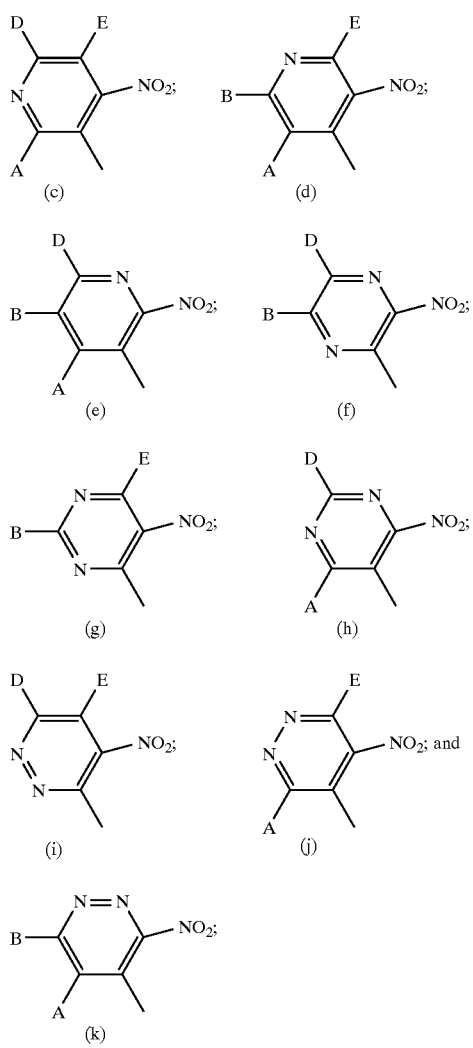

wherein A, B, D and E are as previously defined, and (2) an amine compound having the formula Nitroaryl—$NH_2$, wherein the Nitroaryl moiety is as defined above, in combination with a reagent selected from the group consisting of carbonyldiimidazole, phosgene and triphosgene;

to give a compound having the formula

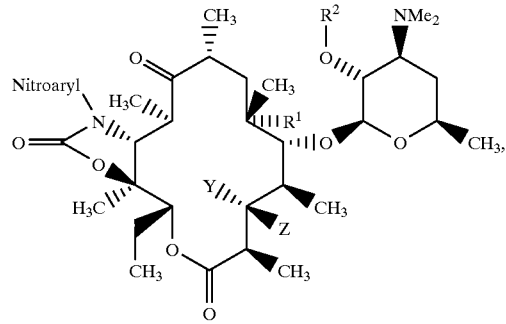

(b) optionally deprotecting;

(c) reducing the nitro group of the Nitroaryl moiety of the compound of step (b) to give a compound having the formula

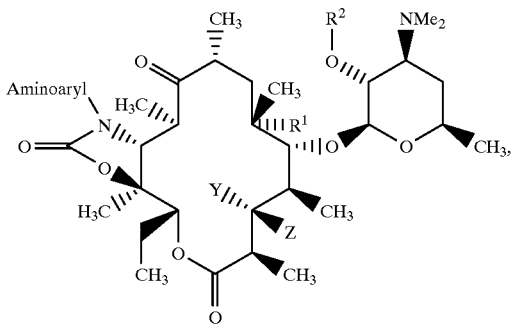

(d) cyclizing the compound of step (c) by treatment with dilute acid to give a compound of a formula (I)–(XI) wherein the optional double bond is present and $R^3$ is absent;

(e) optionally oxidizing the imine nitrogen; optionally reducing the imine; optionally oxiziding the reduced imine nitrogen; optionally derivatizing the reduced imine nitrogen; optionally deprotecting; extracting and isolating the desired compound.

Definitions

The terms "$C_1$–$C_3$-alkyl", "$C_1$–$C_5$-alkyl", "$C_1$–$C_6$-alkyl", or "$C_1$–$C_{12}$-alkyl" as used herein refer to saturated, straight- or branched-chain hydrocarbon radicals containing between one and three, one and five, one and six, or one and twelve carbon atoms, respectively. Examples of $C_1$–$C_3$ alkyl radicals include methyl, ethyl, propyl and isopropyl, examples of $C_1$–$C_5$-alkyl radicals include, but are not limited to, methyl, ethyl, propyl, isopropyl, n-butyl, tert-butyl and neopentyl, examples of $C_1$–$C_6$-alkyl radicals include, but are not limited to, methyl, ethyl, propyl, isopropyl, n-butyl, tert-butyl, neopentyl and n-hexyl, examples of $C_1$–$C_{12}$-alkyl radicals include all of the preceding examples and n-heptyl, octyl, n-decyl, n-undecyl and n-dodecyl, for example.

The term "$C_1$–$C_6$-acyl" as used herein refers to hydrogen atom or a $C_1$–$C_5$-alkyl group, as previously defined, attached to the parent molecular moiety through a carbonyl group. Examples of $C_1$–$C_6$-acyl include, but are not limited to, formyl, acetyl, propionoyl, butanoyl, pentanoyl, hexanoyl.

The term "$C_1$–$C_6$-alkoxy" as used herein refers to an $C_1$–$C_6$-alkyl group, as previously defined, attached to the parent molecular moiety through an oxygen atom. Examples of $C_1$–$C_6$-alkoxy, but are not limited to, methoxy, ethoxy, propoxy, isopropoxy, n-butoxy, tert-butoxy, neopentoxy and n-hexoxy.

The term "$C_1$–$C_3$-alkyl-amino" as used herein refers to one or two $C_1$–$C_3$-alkyl groups, as previously defined, attached to the parent molecular moiety through a nitrogen atom. Examples of $C_1$–$C_3$-alkyl-amino include, but are not limited to methylamino, dimethylamino, ethylamino, diethylamino, and propylamino.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, dichloromethane, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, N.Y., 1986.

The term "aryl" as used herein refers to unsubstituted carbocyclic aromatic groups including, but not limited to, phenyl, 1- or 2-naphthyl and the like.

The term "$C_3$–$C_5$-cycloalkyl- and $C_3$–$C_7$-cycloalkyl" as used herein refers to carbocyclic groups of 3 to 5 or 3 to 7 carbons, respectively, for example, cyclopropyl, cyclobutyl, cyclopentyl, cyclohexyl, and cycloheptyl.

The term "$C_1$–$C_3$-alkyl-$C_3$–$C_5$-cycloalkyl", as used herein refers to a $C_3$–$C_5$-cycloalkyl radical, as defined above, attached to a $C_1$–$C_3$-alkyl radical by replacement of a hydrogen atom on the latter.

The terms "halo" and "halogen" as used herein refer to an atom selected from fluorine, chlorine, bromine and iodine.

The term "halo-$C_1$–$C_3$-alkyl" as used herein refers to a $C_1$–$C_3$-alkyl group as defined above wherein 1, 2 or 3 hydrogen atoms thereon are independently replaced by a halogen atom.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isoxazolyl, thiadiazolyl, oxadiazolyl, thienyl, furanyl, quinolinyl, isoquinolinyl, and the like.

The term "heterocycloalkyl" as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

"Hydroxy-protecting group", as used herein, refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

A the term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, N.Y., 1986.

The term "substituted aryl" as used herein refers to an aryl group as defined herein substituted by independent replacement of one, two or three of the hydrogen atoms thereon with Cl, Br, F, I, OH, cyano, mercapto, nitro, $C_1$–$C_3$-alkyl, halo-$C_1$–$C_3$-alkyl, $C_1$–$C_6$-alkoxy, thio-$C_1$–$C_6$-alkoxy, methoxymethoxy, amino, $C_1$–$C_3$-alkyl-amino, di($C_1$–$C_3$-alkyl-)amino, formyl, carboxy, alkoxycarbonyl, $C_1$–$C_3$-alkyl—CO—O—, $C_1$–$C_3$-alkyl—CO—NH—, or carboxamide; except that tetrafluorophenyl and pentafluorophenyl are also included within the definition of 'substituted aryl."

The term "substituted heteroaryl" as used herein refers to a heteroaryl group as defined herein substituted by independent replacement of one, two or three of the hydrogen atoms thereon with Cl, Br, F, I, OH, $C_1$–$C_3$-alkyl, $C_1$–$C_6$-alkoxy, methoxymethoxy, amino, or $C_1$–$C_3$-alkyl-amino, or may also refer to a mono-oxo substituted heteroaryl compound, such as 4-oxo-1H-quinoline, for example.

The term "substituted heterocycloalkyl" as used herein, refers to a heterocycloalkyl group, as defined above, substituted by independent replacement of one, two or three of the hydrogen atoms thereon with Cl, Br, F, I, OH, cyano, mercapto, nitro, $C_1$–$C_3$-alkyl, halo-$C_1$–$C_3$-alkyl, $C_1$–$C_6$-alkoxy, thio-$C_1$–$C_6$-alkoxy, methoxymethoxy, amino, $C_1$–$C_3$-alkyl-amino, di($C_1$–$C_3$-alkyl-)amino, carboxaldehydo, carboxy, alkoxycarbonyl, $C_1$–$C_3$-alkyl-CO—O—, $C_1$–$C_3$-alkyl—CO—NH—, or carboxamide.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals. without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butryates, acrylates and ethylsuccinates.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol: esters such as ethyl oleate and ethyl laurate; agar; buffering agents such as magnesium hydroxide and aluminum hydroxide; alginic acid; pyrogen-free water; isotonic saline: Ringer's solution: ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oteic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the descriptions of the scheme and the examples that follow are: 9-BBN for 9-borabicyclo[3.3.1]nonane; AIBN for azobisisobutyronitrile; Bu$_3$SnH for tributyltin hydride; CDI for carbonyldiimidazole; DBU for 1,8-diazabicyclo[5.4.0]undec-7-ene; DEAD for diethylazodicarboxylate; DMAP for 4-dimethylaminopyridine; DMF for dimethyl formamide; DPPA for diphenylphosphoryl azide; EtOAc for ethyl acetate; MeOH for methanol; NaHMDS for sodium hexamethyldisilazane; NaN(TMS)$_2$ for sodium bis(trimethylsilyl) amide; NMMO for N-methylmorpholine N-oxide; TEA for triethylamine; THF for tetrahydrofuran; TPP for triphenylphosphine.

Preparation of the Compounds of the Invention

The compounds of the present invention are prepared according to the representative methods described in Schemes 1–5 below.

Scheme 1 illustrates the preparation of compounds (6), which are useful as starting materials for the preparation of compounds of formulas (I)–(XI) wherein R$^1$ is methoxy or O—R, wherein R is as described for compounds of formulas (I)–(XI).

Scheme 1

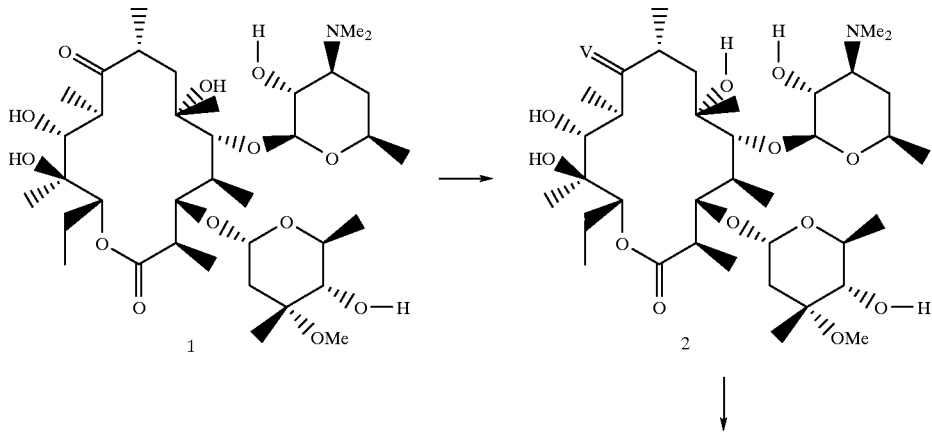

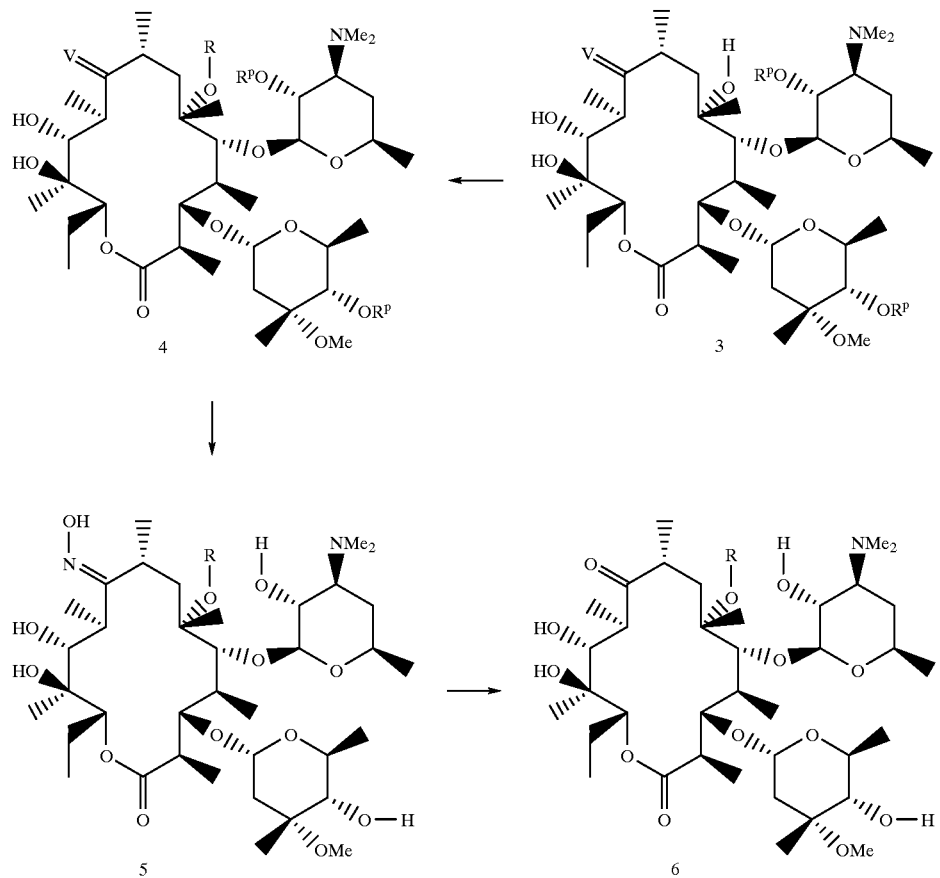

Erythromycin A (1), available from Abbott Laboratories, is first protected at the C-9-carbonyl position to give a compound (2). The preparation of protected erythromycin A is described in the following United States patents, U.S. Pat. No. 4,990,602; U.S. Pat. No. 4,331,803, U.S. Pat. No. 4,680,368, and U.S. Pat. No. 4,670,549 which are incorporated by reference. Also incorporated by reference is European Patent Application EP 260,938. In general, the C-9-carbonyl group of compound (1) is protected as an oxirne, (V is =N—O—$R^{12}$ or =N—O—C($R^{13}$)($R^{14}$)—O—$R^{12}$, wherein $R^{12}$ is selected from the group consisting of (c-1) alkyl of one to six carbon atoms, (c-2) alkyl of one to six carbon atoms substituted with one or more groups selected from the group consisting of (c-2-a) aryl, (c-2-b) substituted aryl, (c-2-c) heteroaryl, (c-2-d) substituted heteroaryl, (c-2-e) heterocycloalkyl, (c-2-f) hydroxy, (c-2-g) alkoxy of one to six carbon atoms, (c-2-h) —$NR^6R^7$ wherein $R^6$ and $R^7$ are as previously defined, and (c-2-i) —$CH_2$—M*—$R^{15}$ wherein M* is selected from the group consisting of —O—, —NH—, —NMe—, —S(O)$_n$— wherein n is 0, 1, or 2, —NHC(O)— and —C(O)—NH—, and $R^{15}$ is selected from the group consisting of —(CH$_2$)$_n$-aryl wherein n is 0, 1, or 2, —(CH$_2$)$_n$-substituted aryl wherein n is 0, 1, or 2, —(CH$_2$)$_n$-heteroaryl wherein n is 0, 1, or 2, —(CH$_2$)$_n$-substituted heteroaryl wherein n is 0, 1, or 2, and —(CH$_2$)$_n$-heterocycloalkyl wherein n is 0, 1, or 2, provided that when the alkyl group is substituted with hydroxy or —$NR^6R^7$ it is of two to six carbon atoms, (c-3) cycloalkyl of three to twelve carbon atoms, (c-4) aryl, (c-5) substituted aryl, (c-6) heteroaryl, and (c-7) substituted heteroaryl. $R^{13}$ and $R^{14}$ are each independently selected from the group consisting of (a) hydrogen, (b) unsubstituted $C_1$-$C_{12}$-alkyl, (c) $C_1$-$C_{12}$-alkyl substituted with aryl, and (d) $C_1$-$C_{12}$-alkyl substituted with substituted aryl, or $R^{13}$ and $R^{14}$ taken together with the carbon to which they are attached form a $C_3$-$C_{12}$-cycloalkyl ring). An especially preferred carbonyl protecting group V is O—(1-isopropoxycyclohexyl) oxime.

The 2'- and 4"-hydroxy groups of (2) are then protected by reaction with a suitable hydroxy protecting reagent, such as those described by T. W. Greene and P. G. M. Wuts in *Protective Groups in Organic Synthesis*, 2nd ed., John Wiley & Son, Inc., 1991, which is incorporated by reference, for example, acetic anhydride, benzoic anhydride, benzyl chloroformate, hexamethyl disilazane, or a trialkylsilyl chloride in an aprotic solvent. Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof. Protection of 2'- and 4"-hydroxy groups of (2) may be accomplished sequentially or simultaneously to provide compound (3) where $R^p$ is a hydroxy protecting group. A preferred protecting group $R^p$ is trimethylsilyl.

The 6-hydroxy group of compound (3) is then alkylated by reaction with an alkylating agent in the presence of base to give compound (4). Alkylating agents include alkyl chlorides, bromides, iodides or alkyl sulfonates. Specific examples of alkylating agents include methyl iodide, allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone, 1,3-dibromo-1-propene, and the like. Examples of alkyl sulfonates are: allyl O-tosylate, 3-phenylpropyl-O-trifluoromethane sulfonate, n-butyl-O-methanesulfonate and the like. Examples of the solvents used are aprotic solvents such as dimethylsulfoxide, diethylsulfoxide, N,N-dimethylformamide, N,N-dimethylacetamide, N-methyl-2-pyrrolidone, hexamethylphosphoric triamide, a mixture thereof or a mixture of one of these solvents with ether, tetrahydrofuran, 1,2-dimethoxyethane, acetonitrile, ethyl acetate, acetone and the like. Examples of the base which can be used include potassium hydroxide, cesium hydroxide, tetraalkylammonium hydroxide, sodium hydride, potassium hydride, potassium isopropoxide, potassium tert-butoxide, potassium isobutoxide and the like.

The deprotection of the 2'- and 4'-hydroxyl groups to give compound (5) is then carried out according to methods described in literature, for example, by T. W. Greene and P. G. M. Wuts in *Protective Groups in Organic Synthesis*, 2nd ed., John Wiley & Son, Inc., 1991, which is incorporated herein by reference. The conditions used for the deprotection of the 2'- and 4'-hydroxyl groups usually results in the conversion of X to =N—OH. For example, using acetic acid in acetonitrile and water results in the deprotection of the 2'- and 4'-hydroxyl groups and the conversion of X from =N—O—R$^{12}$ or =N—O—C(R$^{13}$)(R$^{14}$)—O—R$^{12}$, wherein R$^{12}$, R$^{13}$ and R$^{14}$ are as previously defined, to =N—OH. If this is not the case, the conversion is carried out in a separate step.

The deoximation reaction can be carried out according to the methods described in the literature, for example by Greene (op. cit.) and others. Examples of deoximating agents are inorganic sulfur oxide compounds such as sodium hydrogen sulfite, sodium pyrosulfate, sodium thiosulfate, sodium sulfate, sodium sulfite, sodium hydrosulfite, sodium metabisulfite, sodium dithionate, potassium thiosulfate, potassium metabisulfite and the like. Examples of the solvents used are protic solvents such as water, methanol, ethanol, propanol, isopropanol, trimethylsilanol or a mixture of one or more of the mentioned solvents and the like. The deoximation reaction is more conveniently carried out in the presence of an organic acid such as formic acid, acetic acid and trifluoroacetic acid. The amount of acid used is from about 1 to about 10 equivalents of the amount of compound (5) used. In a preferred embodiment, the deoximation is carried out using an organic acid such as formic acid in ethanol and water to give the desired product (6).

Scheme 2

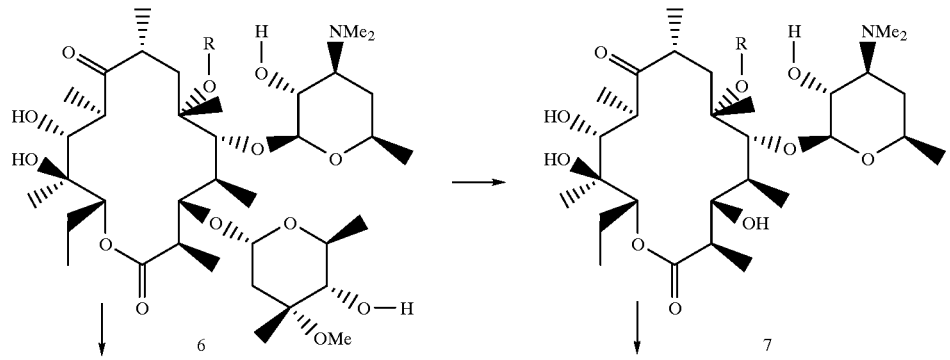

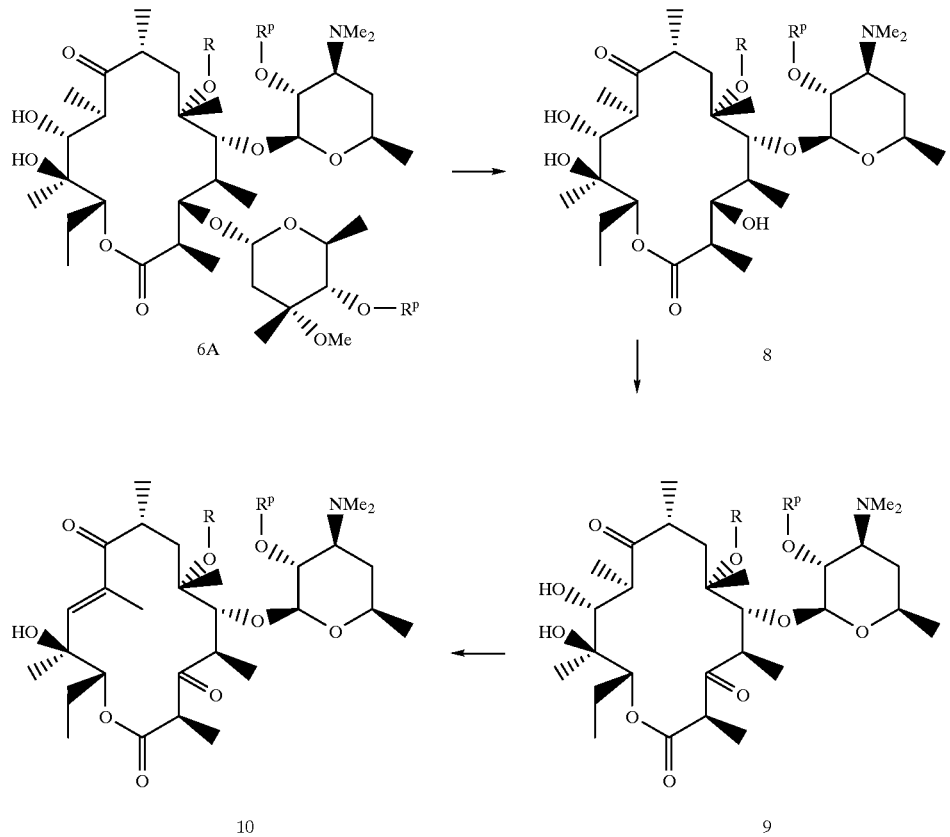

In Scheme 2 are described processes whereby a 6-substituted erythromycin derivative starting material (6) may be converted into the 3-keto derivative (10). The methods are also applicable to 6-deoxy erythromycin (available from Abbot Laboratories) by substituting it for compound (6) thus giving the deoxy anolog of compound (10) which is the intermediate to compounds of formulas (I)–(XI) wherein $R^1$ is H. The cladinose moiety of macrolide (6) may be removed either by mild aqueous acid hydrolysis or by enzymatic hydrolysis to give the descladinose compound (7). Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol and the like. Reaction times are typically 0.5 to 24 hours. The reaction temperature is preferably −10 to 35° C.

The 2′-hydroxy group of (7) is then protected to give compound (8) using a suitable hyroxy protecting reagent such as acetic anhydride, benzoic anhydride, benzyl chloroformate or trialkylsilyl chloride in an aprotic solvent, as defined above, preferably dichloromethane, chloroform, DMF, tetrahydrofuran (THF), N-methyl pyrrolidinone or a mixture thereof. A particularly preferred protecting group $R^P$ is benzoate.

The 3-hydroxy group of compound (8) may oxidized to the ketone (9) using a modified Swern oxidation procedure. Suitable oxidizing agents are N-chlorosuccinimide-dimethyl sulfide or carbodiimide-dimethylsulfoxide. In a typical example, (8) is added into a pre-formed N-chlorosuccinimide and dimethyl sulfide complex in a chlorinated solvent such as methylene chloride at −10 to 25° C. After being stirred for about 0.5 to about 4 hours, a tertiary amine such as triethylamine or Hunig's base is added to produce the corresponding ketone.

Compound (9) may be dehydrated at the 11-hydroxy position by treatment with, for example, refluxing ethylene carbonate in triethylamine or ethylene carbonate heated in DMF in the presence of an inorganic base such as $K_2CO_3$, to form compound (10) having a C10–C11 double bond. Alternatively, (9) may be converted to its corresponding 11-O-mesylate by reaction with methanesulfonic anhydride in pyridine, and the mesylate is then converted to (10) by treatment with an amino base such as 1,8-diazobicyclo [5.5.0]undec-7-ene (DBU) in acetone or acetonitrile.

In an alternate dehydration reaction, the method follows the procedure described by Baker et al., *J. Org. Chem.*, 1988, 53, 2340, which is incorporated herein by reference. In particular, the 2′-protected ketolide derivative (9), is converted to an intermediate cyclic carbonate (not shown) by reaction with carbonyldiimidazole and sodium hexamethyldisilazide. Cyclic carbonates may also prepared from (9) by reaction with sodium hydride or lithium hydride and phosgene, diphosgene or triphosgene under anhydrous conditions followed by aqueous work up. The cyclic carbonate may then be dehydrated by treatment with an amine base such as DBU in a solvent such as benzene or acetonitrile.

Also shown in Scheme 2 is an alternate procedure for preparing compound (8), namely first protecting the 2′ and 4″ hydroxy groups of compound (6) by the procedures described above to give a compound (6A). Compound (6A)

may then be converted to the desired compound (8) by hydrolytic removal of the protected cladinose moiety by treatment with acid as described above.

Scheme 3 illustrates the conversion of the fully protected compound (6A) to the $C_{10}$–$C_{11}$ unsaturated macrolide (11). This conversion may be accomplished by the procedures described for Scheme 2 for converting compound (9) into compound (10). The reaction is also applicable to the 6-deoxy analog of (6A).

As shown in Scheme 4, compound (8) may be protected at the 3-hydroxy position by means of a hydroxy protecting reagent as discussed earlier to give compound (12) Compound (12) may then be converted to compound (13) by the procedures described in Scheme 2 above for converting compound (9) to compound (10).

Also, compound (8) may be converted to the desoxy compound (14) by treatment with an excess of NaH in an aprotic solvent at from about 0 to −30° C. under an inert atmosphere, followed by reaction of the intermediate anion (not shown) with $CS_2$ and ($CH_3I$ at about −5 to 10° C., to form a 3-O-xanthyl compound. This xanthate intermediate (not shown) is then reacted with about 1.1 to 1.3 equivalents of $Bu_3SnH$ under an inert atmosphere in the presence of a catalytic amount of AIBN or other suitable radical initiator to afford the desired compound (14). This reaction is performed in a solvent suitable for a free radical reaction, such as benzene or toluene, for example, at reflux conditions. Compound (14) may then be converted to compound (15) by the procedures described in Scheme 2 above for converting compound (9) to compound (10). The reaction is also applicable to prepare the 6-deoxy analog of (15).

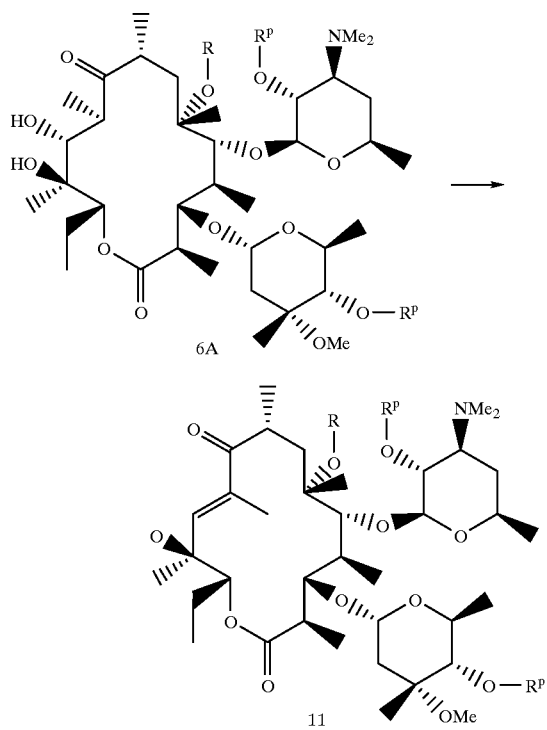

Scheme 3

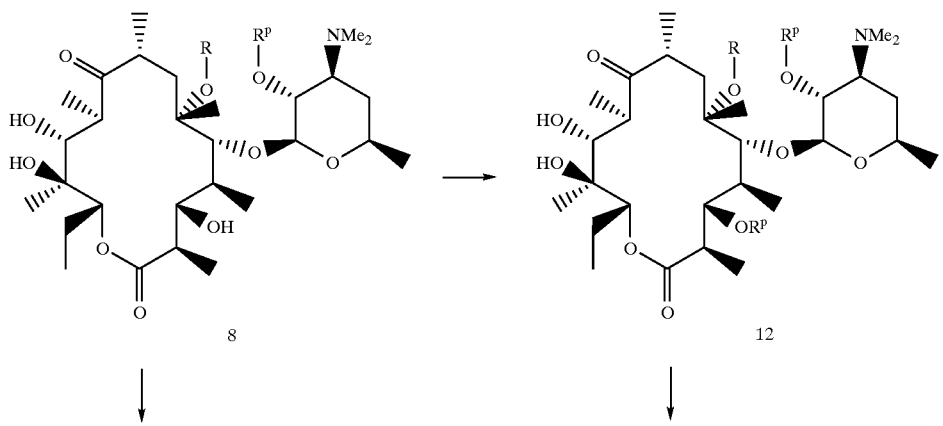

Scheme 4

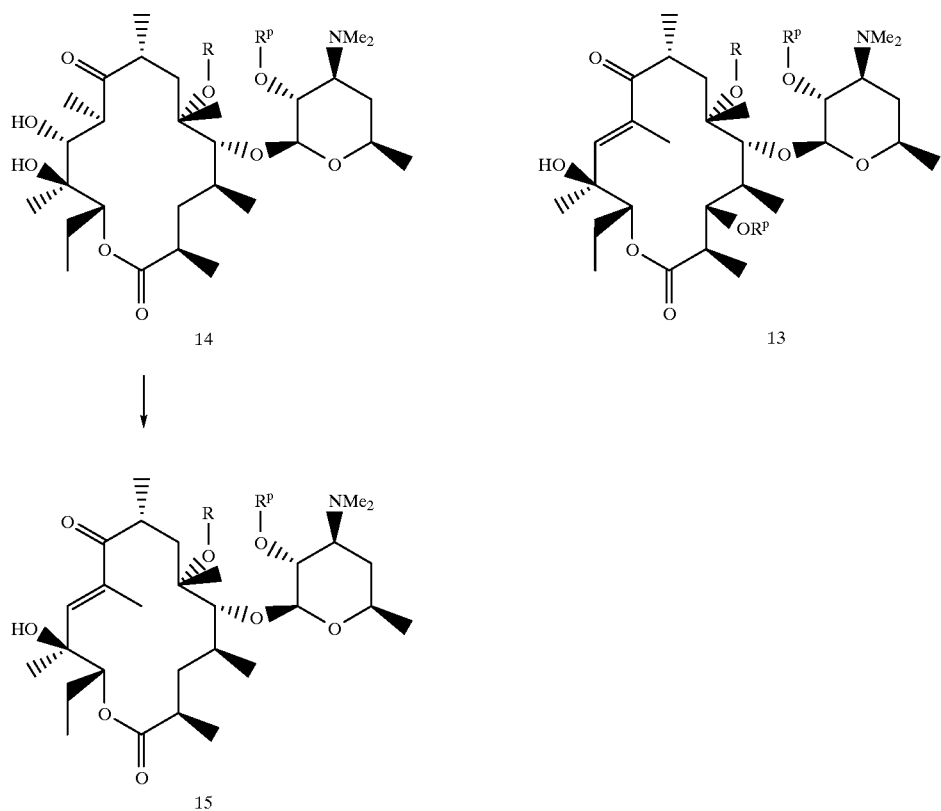
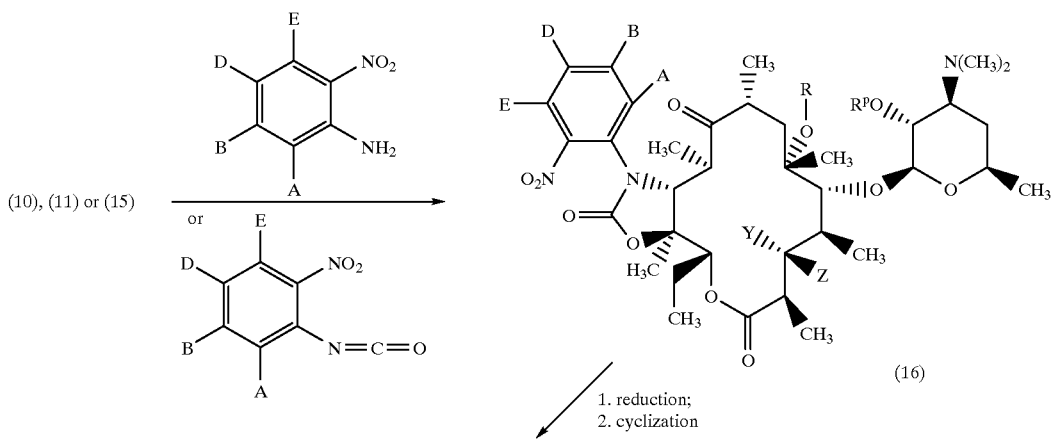
Scheme 5

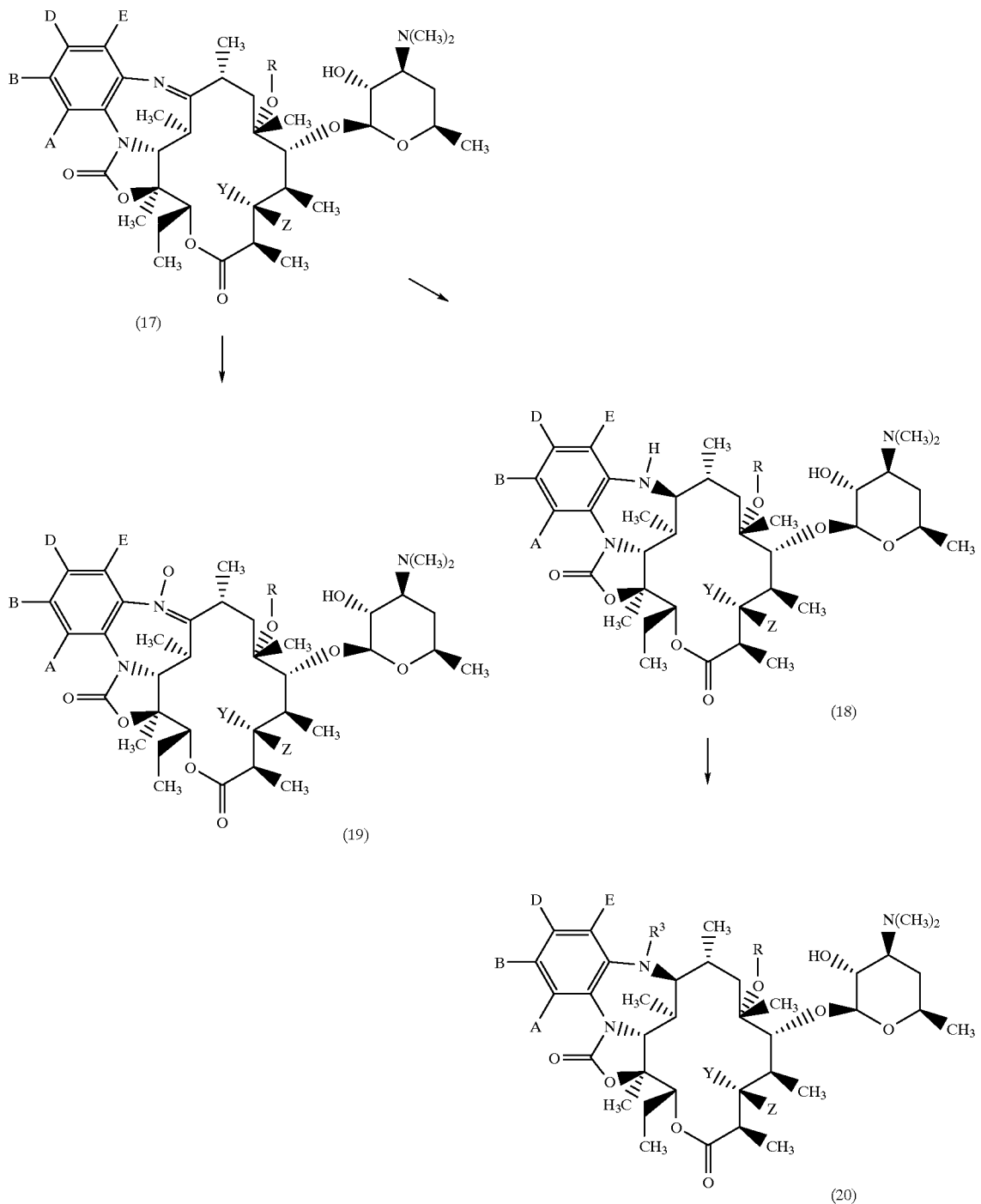

Scheme 5 describes the procedures by which compounds (10), (11) or (15), or 6-deoxy analogs thereof, may be converted into the desired compounds of the invention. Although Scheme 5 is illustrated with an appropriately 1,2-substituted benzene compound as the reagent, thereby forming a compound of Formula (I) wherein A, B, D and E are H, this reaction may be carried out with any of the appropriately substituted precursor heteroaryl compounds that may be required to form compounds having structures of the formulas (II)–(XI), wherein A, B, D and E are as defined for those compounds. These appropriately substituted heteroaryl compounds must have a nitro group adjacent to either an amino or isocyanato group. Examples of such compounds include, but are not limited to, 2-nitroaniline, 2-amino-3-nitropyridine, 4-methyl-2-nitrophenylisocyanate, 4-methoxy-2-nitroaniline, 4-amino-3-nitrobenzonitrile, 2-nitrophenylisocyanate, 2-amino-3-nitropyridine, 3-amino-4-nitropyridine, 4-amino-3-nitropyridine, 3-amino-2-nitropyridine, 2-amino-3-nitropyrazine, 4-amino-5-nitropyrimidine, 5-amino-4-nitropyrimidine, 3-amino-4-nitropyridazine, 4-amino-5-nitropyridazine, 4-amino-3-nitropyridazine, 2-isocyanato-3- nitropyridine, 3-isocyanato-4-nitropyridine, 4-isocyanato-3-nitropyridine, 3-isocyanato-2-nitropyridine, 2-isocyanato-3-nitropyrazine, 4-isocyanato-5-nitropyrimidine, 5-isocyanato-4-nitropyrimidine, 3-isocyanato-4-nitropyridazine, 4-isocyanato-5-nitropyridazine, and 4-isocyanato-3-nitropyridazine.

Compounds (10), (11) or (15) are suitable starting materials for the preparation of compounds (I)–(XI). When the starting material is compound (11) it is preferably protected at the 4"-hydroxy position before treating as described below. A suitable hydroxy protecting group may be selected as described in Scheme 2, and optionally removed as the last step following the procedures described below.

Compounds (10), (11) or (15) are first treated with a base, such as sodium hydride, lithium hydride, DMAP, or the like, followed by either of two reagents to give the compounds (16), wherein $R^1$, $R^2$, Y and Z are as described above. One reagent consists of a 2-nitro substituted aryl isocyanate. When a hydride base is used, the reaction is preferably performed at from about 0° C. to room temperature and in the presence of CuI; when DMAP is used, the reaction temperature may be from room temperature to reflux temperature. The other reagent consists of a 2-nitro substituted aryl amine in combination with carbonyldiimidazole which react to form the intermediate isocyanate in situ, which is then reacted with compounds (10), (11) or (15). The reaction may be performed from room temperature to reflux temperature. The reactions for forming (16) are performed under anhydrous conditions in an aprotic solvent, which does not adversely affect the reaction, for example, dichloromethane, chloroform, xylenes, DMF, tetrahydrofuran (THF), N-methyl pyrrolidinone or mixtures thereof.

Compounds (16) are first deprotected at the 2'-hydroxy group by stirring with methanol for about 1 to 4 days. The nitro group of the deprotected compounds (not shown) is then reduced to an amino group in the presence of mild acid, such as with Pd/C in methanol and acetic acid, or with Zn/HCl in methanol. The amino intermediates are then cyclized to give the tricyclic compounds (17), which are compounds of formula (I) of the invention. The cyclization may occur under the reduction conditions, but isolation and treatment of the amine with mild acid and heat, such as with acetic acid in refluxing ethanol, may also be necessary. Compounds (17) may be reduced at the imine position with a borohydride reducing agent, such as sodium cyanoborohydride, to give compounds (18), which are also compounds of the invention. Compounds (17) may be treated with an oxidizing reagent to give the N-oxide compounds (19). Compounds (18) may be treated with an oxidizing reagent to give the compounds (20), wherein $R^3$ is oxygen. Alternately, compounds (18) may be treated with an $C_1$–$C_6$-alkylating reagent, wherein the alkyl group is optionally substituted with halogen, aryl or heteroaryl. Suitable alkylating reagents include, but are not limitied to methyl iodide, ethyl bromide, propyl chloride, butyl bromide, pentyl iodide, hexyl bromide, benzyl bromide, trifluoromethyl iodide, and 2-(4-pyridyl)ethyl bromide. Additionally, reductive alkylation in the presence of a borohydride reducing agent and an alkyl aldehyde may be used.

Although compound (13) may be converted to the desired compound (17) wherein Y is H and Z is hydroxy by the procedure described in Scheme 5, the preferred route to the preparation of these compounds is to first prepare the compound (17) wherein Y is H and Z is cladinose, then hydrolytically remove the cladinose moiety with acid treatment as described previously.

The desired compounds of the invention may be prepared directly as described above in Schemes 1–5 above or obtained from chemical modification of an initially prepared 6-O-substituted compound. Representative examples of further elaboration of the 6-O-substitient position are shown in Scheme 6. For example, compound (17) where R is 6-O—$CH_2CH=CH_2$ and $M^1$ represents the macrolide ring system can be further derivatized. The double bond of the allyl compound can be (a) reduced to give the 6-O-propyl compound (27); (b) treated with osmium tetroxide to give the 2,3-dihydroxypropyl compound (31) which in turn may be functionalized at the primary hydroxyl group to give (32) wherein R* is $C_1$–$C_3$-alkyl or $C_1$–$C_3$-alkoxy-$C_1$–$C_3$-alkyl; (c) oxidized with m-chloroperoxybenzoic acid to give the epoxy methyl compound (29) which can be opened with nucleophilic compounds, for example, amines or N-containing heteroaryl compounds, to give compounds with N-containing side chains (30); (d) oxidized under Wacker conditions as described by Henry in "Palladium Catalyzed Oxidation of Hydrocarbons", Reidel Publishing Co., Dordrecht, Holland (1980), to cive the 6-O—$CH_2$—C(O)—$CH_3$ compound (28); and (e) ozonized to give the aldehyde (21) which can in turn be (a) converted to oximes (22) and (24) by reaction with $H_2NOR^5$ or $H_2NOH$ respectively, or (b) reductively Scheme 6

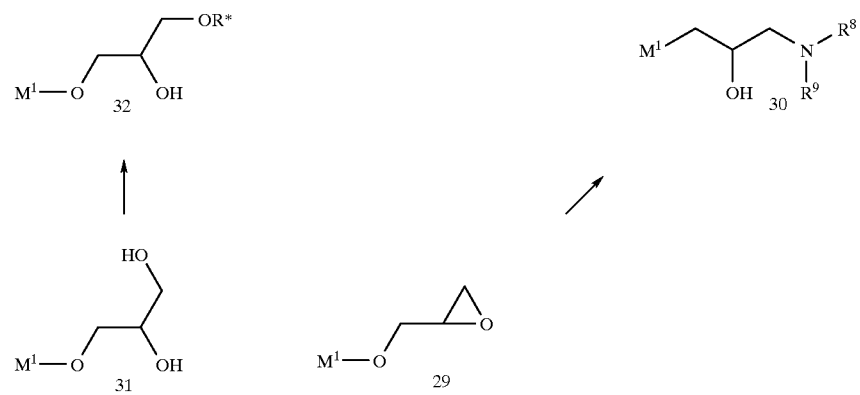

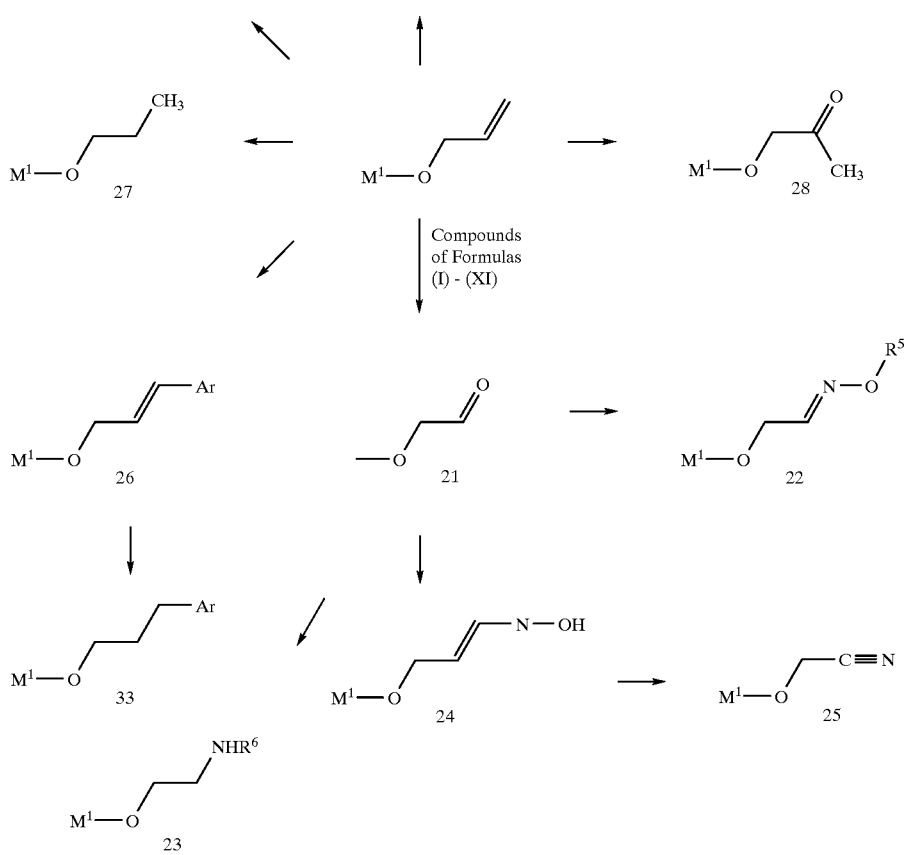

aminated to give the amine (23). Reaction of the oxime (24) with diisopropyl carbodiimide in the presence of CuCl gives the nitrile (25). Reaction of (17) with an aryl halide under Heck conditions (Pd(II) or Pd(0), phosphine, and amine or inorganic base, see *Organic Reactions*, 1982, 27, 345–390) gives (26). Reduction of the double bond in (26), for example using $H_2$ and palladium on carbon gives (33).

The foregoing may be better understood by reference to the following examples which are presented for illustration and not to limit the scope of the inventive concept.

EXAMPLES

The procedures described above for preparing the compounds of the present invention will be better understood in connection with the following examples, which are intended as an illustration of and not a limitation upon the scope of the invention. Various changes and modifications to the disclosed embodiments will be apparent to those skilled in the art. Such changes and modifications, including without limitation those relating to the chemical structures, substituents, derivatives, interrnediates, syntheses, formulations and/or methods of use of the invention, may be made without departing from the spirit and scope thereof.

The NMR data for the central portion of selected compounds exemplified below are given in Table 2, which is placed after Example 20.

Example 1

Preparation of Starting Material:

Compound (10) from Scheme 2; R is methyl; $R^p$ is benzoyl

Step 1a. Compound (7) of Scheme 2, R is methyl

A sample of clarithromycin (Compound (6) of Scheme 2, R is methyl (Abbott Labs, 900 g, 1.2 mole)) was suspended in water (10.8 L) and ethanol (4.0 L), and the resulting slurry was stirred at room temperature until homogeneous (about 20 minutes). HCl (1.00M, 2.16 L) was added over 15 minutes, and the reaction mixture was stirred for 20 hours. NaOH solution (2.00M, 1.20 L) was added over 30 minutes until pH 10.5–11.0 was reached, and the reaction mixture was stirred for 2 hours. The precipitate was collected and washed with cold water, which was dried under vacuum at 50° C. to afford 601 g of the title compound. MS m/z $(M+H)^+$: 590.

Step 1b. Compound (8) of Scheme 2, R is methyl, $R^p$ is benzoyl

To a solution of the compound from Step 1a, (600 g, 1.01 mole) in methylene chloride (2.0 L) was added 90% technical grade benzoic anhydride (380 g, 1.59 mol). Triethylamine (222 mL, 1.59 mol) was added over 10 minutes, and the thick solution was stirred for 48 hours. Sodium bicarbonate solution (10%, 1.5 L) was added, and the mixture was stirred for 30 minutes. The layers were separated, and the organic fraction was washed with water (3×600 mL) and brine (600 mL). The organic layer was dried ($Na_2SO_4$) and filtered, and the volatiles were removed on a rotary evaporator to leave a syrup. Trituration with a warm solution of hexane (2.0 L) and ethyl acetate (100 mL) converted the product to white crystals. The product was filtered, washed with hexane and dried in a vacuum oven overnight at ambient temperature to give the title compound (691 g). MS m/z (M+H)+: 694.

Step 1c. Compound (9) of Scheme 2, R is methyl, $R^p$ is benzoyl

A sample of N-chlorosuccinimide (57.0 g, 0.42 mol) was slurried in anhydrous methylene chloride (600 mL), and dimethyl sulfide (36.0 mL, 0.49 mol) was added dropwise over 30 minutes. A sample of the compound from Step 1b (200.0 g, 0.29 mol) was dissolved in methylene chloride (1.20 L), and this solution was added to the reaction mixture over 45 minutes. After stirring for 30 minutes a solution of triethylamine (40.0 mL) in methylene chloride (200 mL) was added dropwise over 30 minutes at 0° C. under nitrogen. The resulting solution was washed with sodium bicarbonate (10%, 3×600 mL) and brine (600 mL). The organic fraction was dried ($Na_2SO_4$) and filtered, and the volatiles were removed on a rotary evaporator to give a thick syrup, which became a solid upon standing. The solid was crushed and dried overnight at ambient temperature in a vacuum oven to give the title compound (196 g). MS m/z (M+H)+: 692.

Step 1d. 11-O-methanesulfonyl Derivative of the Compound (9) of Scheme 2, R is methyl, $R^p$ is benzoyl To a solution of the compound from Step 1c above (20.00 g, 28.9 mmole) in pyridine (40 mL) cooled to 0° C. and held under $N_2$ was added methanesulfonic anhydride (14.6 g, 83.81 mmole), and the reaction was allowed to stir at room temperature for 17 hours. The pyridine was removed under vacuum, and the residue was dissolved in EtOAc (400 mL). This solution was washed with saturated aqueous $NaHCO_3$, $H_2O$ and brine, dried ($MgSO_4$), decolorized with charcoal, and filtered through a diatomaceous earth filter aid. The solvent was removed under vacuum to afford the crude product (24.46 g). This material was taken directly to the next step without further purification.

Step 1e. Compound (10) of Scheme 2, R is methyl, $R^p$ is benzoyl

The mesylate from Step 1d above was dissolved in acetone (70 mL), and DBU (5.22 mL, 34.9 mmole) added. After stirring at room temperature for 22 hours the acetone was removed under vacuum, EtOAc (250 mL) was added, and the organic layer was washed with 100-mL portions of sat. aq. $NaHCO_3$, $H_2O$, and brine. The solution was dried ($MgSO_4$), decolorized with charcoal and filtered through a diatomaceous earth filter aid. The solvent was removed under vacuum to afford the crude product (18.54 g). This material was purified by chromatography on silica gel, eluting with 40% ethyl acetate/hexanes containing 0.25 % concentrated $NH_4OH$. The appropriate fractions were combined and concentrated to give the product. MS m/z (M+H)+: 674.

Example 2

Compound of Formula (I): $R^1$ is methoxy; $R^2$ is H, $R^3$ is Absent, the Double Bond is Present, A, B, D and E are H, and Y and Z Taken Together with the Atom to which they are Attached Form an Oxo Group Step 2a. Compound (16) of Scheme 5, R is methyl, $R^p$ is benzoyl, A, B, D and E are H, and Y and Z Taken Together with the Atom to which they are Attached Form an Oxo Group NaH (392 mg, 9.80 mmol, 60% dispersion in hexanes) was placed in the reaction vessel and washed (3×) with hexanes. To the washed NaH was added THF, and the solution was cooled to 0° C. under nitrogen. To this solution was added a sample of the compound from Example 1 above (3.00 g, 4.45 mmol) in two portions. The solution was stirred for 10 minutes, then 2-nitrophenylisocyanate (1.46 g, 8.90 mmol, Aldrich) and Cu(I)Cl (146 mg, 1.47 mmol) were added. The reaction mixture was then stirred at room temperature for 16 hours. The reaction was quenched by addition of aqueous 10% ammonium hydroxide in saturated ammonium chloride solution. The mixture was extracted with ether, and the organic layer was washed with water and brine and dried over $Na_2SO_4$. The solvent was removed, and the residue was purified by flash chromatography on silica gel, eluting with 30% acetone/hexane to afford 1.58 g of the title compound. MS m/z: 838 (M+H)+.

Step 2b, Compound (16) of Scheme 5, R is methyl; $R^p$ is H; A, B, D and E are H The material from Step 2a was dissolved in methanol (50 mL) and stirred at room temperature under nitrogen for 48 hours. The solvent was removed, and the residue was purified by flash chromatography on silica gel, eluting with 4:95:1–5:94:1 methanol/dichloromethane/$NH_4OH$ to afford 0.94 g of the title compound. MS m/z: 734 (M+H)+.

Step 2c. Compound of Formula (I): $R^1$ is methoxy; $R^2$ is H, $R^3$ is Absent, the Double Dond is Present, A, B, D and E are H, and Y and Z Taken Together with the Atom to which they are Attached Form an Oxo Group To a sample (530 mg) of the compound from Step 2b in 10:1 methanol/acetic acid (16.5 mL) was added 10% Pd/C (250 mg), and the mixture was stirred for 23 hours under 1 atm of hydrogen. The catalyst was removed, and the mixture was partitioned between 1N NaOH and ethyl acetate. The organic phase was washed with with water and brine and dried over $Na_2SO_4$. The solvent was removed, and the residue was purified by flash chromatography on silica gel, eluting with 5:94:1 methanol/dichloromethane/$NH_4OH$ to afford 391 mg of the title compound. MS m/z: 686 (M+H)+. Anal. Calcd. for $C_{37}H_{55}N_3O_9$: C, 64.80; H, 8.08; N, 6.13; Found: C, 64.41; H, 8.06; N, 6.09.

Example 3

Compound of Formula (I): $R^1$ is methoxy; $R^2$ is H, $R^3$ is H, the Double Bond is Absent, A, B, D and E are H, and Y and Z Taken Together with the Atom to which they are Attached Form an Oxo Group A sample of the compound from Example 2 (229 mg) was stirred in methanol (7 mL), and sodium cyanoborohydride (87 mg) and bromocresol green indicator were added. To this mixture acetic acid was added dropwise until the indicator was pale green. The mixture was stirred for 6.5 hours, then quenched by pouring it into saturated aqueous sodium bicarbonate solution. The mixture was then extracted with ethyl acetate, and the organic phase was washed with with water and brine and dried over $Na_2SO_4$. The solvent was removed, and the residue was purified by flash chromatography on silica gel, eluting with 5:94:1 methanol/dichloromethane/$NH_4OH$ to afford 222 mg of the title compound. MS m/z: 688 (M+H)+. Anal. Calcd. for $C_{37}H_{57}N_3O_9$: C, 64.60; H, 8.35; N, 6.11; Found: C, 64.68; H, 8.49; N, 5.90.

Example 4

Compound of Formula (I): $R^1$ is methoxy; $R^2$ is H, $R^3$ is Absent, the Double Bond is Present, A, B, and E are H, D is methyl, and Y and Z Taken Together with the Atom to which they are Attached Form an Oxo Group Step 4a. Compound (16) of Scheme 5, R is methyl; $R^p$ is benzoyl, A, B, and E are H, D is methyl To a sample of the compound from Example 1 (1.02 g, 1.52 mmol) was added DMAP (182 mg, 1.49 mmol), 4-methyl-2-nitrophenylisocyanate and toluene (10 mL). The reaction mixture was stirred at reflux for 17 hours, additional isocyanate reagent (100 mg) was added, and the mixture stirred at reflux for 26 hours. The reaction was cooled and extracted wtih ethyl acetate. The organic layer was washed with water and brine and dried over $Na_2SO_4$. The solvent was removed, and the residue was purified by flash chromatography on silica gel, eluting with 30% acetone/hexane to afford 900 mg of the title compound.

Step 4b. Compound of Formula (I): $R^1$ is methoxy; $R^2$ is H, $R^3$ is Absent, the Double Bond is Present, A, B, and E are H, D is methyl, and Y and Z Taken Together with the Atom to which they are Attached Form an Oxo Group Following the procedures of Example 2, steps b and c, the title compound was prepared. MS m/z: 700 (M+H)$^+$. Anal. Calcd. for $C_{38}H_{57}N_3O_9$: C, 65.21; H, 8.21; N, 6.00; Found: C, 65.00; H, 8.42; N, 5.96.

Example 5

Compound of Formula (I): $R^1$ is methoxy; $R^2$ is H, $R^3$ is absent, the Double Bond is Present, A, B, and E are H, D is methoxy, and Y and Z Taken Together with the Atom to which they are Attached Form an Oxo Group Step 5a. Compound (16) of Scheme 5, R is methyl; $R^p$ is benzoyl, A, B, and E are H, D is methoxy A sample of carbonyldiimidazole (724 mg, 4.47 mmol) and DMAP (544 mg, 4.46 mmol) were suspended in dry xylenes (30 mL), and 4-methoxy-2-nitroaniline (749 mg, 4.46 mmol) was added. The mixture was stirred under nitrogen at reflux for 2 hours, then cooled to 50° C. To this solution was added a sample of the compound from Example 1 (1.00 g, 1.49 mmol), and the mixture was heated at 125° C. overnight. The mixture was cooled and extracted with ethyl acetate. The organic layer was washed with water and brine and dried over $Na_2SO_4$. The solvent was removed, and the residue was purified by flash chromatography on silica gel, eluting with 30% acetone/hexane to afford 580 mg of the title compound. MS m/z: 764 (M+H)$^+$.

Step 5b. Compound of Formula (I): $R^1$ is methoxy; $R^2$ is H, $R^3$ is Absent, the Double Bond is Present, A, B, and E are H, D is methoxy, and Y and Z Taken Together with the Atom to which they are Attached Form an Oxo Group Following the procedures of Example 2, Steps b and c, the title compound (311 mg) was prepared from a 430 mg sample of the compound of Step 5a. MS m/z: 716 (M+H)$^+$. Anal. Calcd. for $C_{38}H_{57}N_3O_{10}$: C, 63.76; H, 8.03; N, 5.87; Found: C, 63.61; H, 7.81; N, 5.77.

Example 6

Compound of Formula (I): $R^1$ is methoxy; $R^2$ is H, $R^3$ is Absent, the Double Bond is Present, A, B, and E are H, D is cyano and Y and Z Taken Together with the Atom to which they are Attached Form an Oxo Group Following the procedure of Example 5 Step a, except substituting 4-cyano-2-nitroaniline for the 4-methoxy-2-nitroaniline thereof, then treating with methanol according to Example 2 Step b, then treating the deprotected compound with Zn and hydrochloric acid in methanol at room temperature for 19 hours, and purifiying the product by flash chromatography on silica gel, eluting with 95:5:0.1 dichloromethane/methanol/ammonium hydroxide, the title compound was prepared (225 mg). MS m/z: 711 (M+H)$^+$. Anal. Calcd. for $C_{38}H_{54}N_4O_9$: C, 64.21; H, 7.66; N, 7.88; Found: C, 64.04; H, 7.78; N, 775

Example 7

Compound of Formula (II): $R^1$ is methoxy; $R^2$ is H, $R^3$ is Absent, the Double Bond is Present, B, D and E are H, and Y and Z Taken Together with the Atom to which they are Attached Form an Oxo Group Following the procedures of Example 5, except substituting 2-amino-3-nitropyridine for the 4-methoxy-2-nitroaniline thereof, the title compound was prepared (200 mg) . MS m/z: 687 (M+H)$^+$.

Example 8

Compound of Formula (I): $R^1$ is allyloxy; $R^2$ is H, $R^3$ is Absent, the Double Bond is Present, A, B, D and E are H, and Y and Z Taken Together with the Atom to which they are Attached Form an Oxo Group A compound of formula (10) of Scheme 2, wherein R is allyl, (10 g) was treated according to the procedures of Steps 1d and 1e of Example 1 to give a compound of formula (11) of Scheme 3. This latter compound (1.04 g) was treated with 2-nitroaniline according to the procedure of Step 5a of Example 5, and the resulting compound (0.62 g) was first deproteded at the 2'-position with methanol according to the method of example 2 Step b, then treated with Zn and HCl in methanol for 20 hours at room temperature. The mixture was extracted with ethyl acetate, and the organic layer was washed with water and brine and dried over $Na_2SO_4$. The solvent was removed, and the residue was purified by flash chromatography on silica gel. eluting with 95:5:0.1 dichloromethan/methanol/ammonium hydroxide, the title compound was prepared (166 mg). MS m/z: 712 (M+H)$^+$. Anal. Calcd. for $C_{39}H_{57}N_3O_9$: C, 65.80; H, 8.07; N, 5.90; Found: C, 65.46; H, 8.07; N, 5.76

The starting material (compound of formula (10) of Scheme 3, wherein R is allyl) was prepared as follows:

Step 8a. 6-O-allyl-2',4"-bis-O-trimethylsilylerythromycin A 9-[O-(1-isopropoxycyclohexyl)oxime (Compound (4) of Scheme 1, R is allyl, Rp is trimethylsilyl, V is N-O-(1-isopropoxycyclohexyl)

To a 0° C. solution of 2',4"-bis-O-trimethylsilylerythromycin A 9-[O-(1-isopropoxycyclohexyl)oxime (1.032 g, 1.00 mmol), prepared according to the method of U.S. Pat. No. 4,990,602) in 5 mL of DMSO and 5 mL of THF was added freshly distilled allyl bromide (0.73 mL, 2.00 mmol). After approximately 5 minutes, a solution of potassium tert-butoxide (1M 2.0 mL, 2.0 mL) in 5 mL of DMSO and 5 mL of THF was added dropwise over 4 hours. The reaction mixture was taken up in ethyl acetate and washed with water and brine. The organic phase was concentrated in vacuo to give the desired compound (1.062 g) as a white foam.

Step 8b. 6-O-allyl-erythromycin A 9-oxime (Compound (5) of Scheme 1, R is allyl)

To a solution of the compound resulting from Step 8a (1.7 g) in 17 mL of acetonitrile and 8.5 mL of water was added 9 mL of acetic acid at ambient temperature. After several hours at ambient temperature, the reaction mixture was diluted with 200 mL of toluene and concentrated in vacuo. The residue obtained was found to contain unreacted starting material, so additional acetonitrile (15 mL), water (70 mL) and HOAc (2 mL) was added. After 2 hours, an additional 1 mL aliquot of HOAc was added. After approximately three more hours, the reaction mixture was placed in the freezer overnight. The reaction mixture was allowed to warm to ambient temperature, diluted with 200 mL of toluene and concentrated in vacuo. The residue was chased twice with toluene and dried to constant weight (1.524 g).

Step 8c 6-O-allyl erythromycin A (Compound (6) of Scheme 1, R is allyl)

The compound resulting from Step 8b (1.225 g) in 16 mL of 1:1 ethanol-water was treated with $NaHSO_3$ (700 mg) and formic acid (141 µL) and warmed at 86° C. for 2.5 hours. The reaction mixture was allowed to cool to ambient temperature, diluted with 5–6 mL of water, basified with 1N NaOH to pH 9–10 and extracted with ethyl acetate. The combined organic extracts were washed with brine (2×), dried over $MgSO_4$, filtered and concentrated in vacuo. The crude material was purified by column chromatography eluting with 1% MeOH in methylene chloride containing 1% ammonium hydroxide to give 686 mg (57%) of the title compound. $^{13}$C NMR ($CDCl_3$) δ 219.3 (C-9), 174.8 (C-1), 135.5 (C-17), 116.3 (C-18), 101.9 (C-1'), 95.9 (C-1"), 79.7 (C-5), 78.8 (C-6), 78.5 (C-3), 74.1 (C-12), 72.4 (C-3"), 70.6 (C-11), 68.1 (C-5'), 65.5 (C-16), 65.1 (C-2'), 49.0 (C-3" O—$CH_3$), 45.0 (C-2), 44.1 (C-8), 39.7 ($NMe_2$), 37.9 (C-4), 37.1 (C-10), 34.6 (C-2"), 28.4 (C-4'), 21.0, 20.6 (C-3" $CH_3$, C-6' $CH_3$), 20.8 (C-14), 18.3 (C-6"), 18.1 (C-8 $CH_3$), 15.7, 15.6 (C-2 $CH_3$, C-6 $CH_3$), 11.9 (C-10 $CH_3$), 10.1 (C-15), 8.9 (C-4 $CH_3$). MS (FAB)+ m/e 774 $(M+H)^+$, 812 $(M+K)^+$.

Step 8d: 6-O-allyl-3-O-descladinose erythromycin A (Compound (7) of Scheme 2, R is allyl)

To a suspension of the compound prepared in Step 8c (7.73 g, 10.0 mmol) in ethanol (25 mL) and water (75 mL) was added aqueous 1M HCl (18 mL) over 10 minutes. The reaction mixture was stirred for 9 hours at ambient temperature and then was left standing in the refrigerator overnight. Aqueous 2M NaOH (9 mL, 18 mmol) which resulted in the formation of a white precipitate. The mixture was diluted with water and filtered. The solid was washed with water and dried under vacuum to give the descladinosyl compound 7 (3.11 g).

Step 8e: 6-O-allyl-2'-benzoyl-3-O-descladinose erythromycin A (Compound (8) of Scheme 2, R is allyl, Rp is benzoyl)

To a solution of the product of Step 8d (2.49 g, 4.05 mmol) in dichloromethane (20 mL) was added benzoic anhydride (98%, 1.46 g, 6.48 mmol) and triethylamine (0.90 mL, 6.48 mmol) and the white suspension was stirred for 26 hours at ambient temperature. Aqueous 5% sodium carbonate was added and the mixture was stirred for 20 minutes. The mixture was extracted with dichloromethane. The organic phase was washed with aqueous 5% sodium bicarbonate and brine, dried over sodium sulfate and concentrated in vacuo to give a white foam. Chromatography on silica gel (30% acetone-hexanes) gave the title compound (2.46 g) as a white solid.

Step 8f: 6-O-allyl-2'-benzoyl-3-oxo 3-O-descladinose erythromycin A (Compound (9) of Scheme 3, R is allyl, Rp is benzoyl)

To a −10° C. solution under $N_2$ of N-chlorosuccinimide (0.68 g, 5.07 mmol) in dichloromethane (20 mL) was added dimethylsulfide (0.43 mL, 5.92 mmol) over 5 minutes. The resulting white slurry was stirred for 20 minutes at −10° C. and then a solution of the compound resulting from Step 8e (2.43 g, 3.38 mmol) in dichloromethane (20 mL) was added and the reaction mixture was stirred for 30 minutes at −10 to −5° C. Triethylamine (0.47 mL, 3.38 mmol) was added dropwise over 5 minutes and the reaction mixture was stirred for 30 minutes at 0° C. The reaction mixture was extracted with dichloromethane. The organic phase was washed twice with aqueous 5% sodium bicarbonate and once with brine, dried over sodium sulfate, and concentrated in vacuo to give a white foam. Chromatography on silica gel (30% acetone-hexanes) gave the title compound (2.27 g) as a white foam.

Step 8g: 6-O-allyl 2'-benzoyl 3-oxo 3-O-descladinose erythromycin A (Compound (10) of Scheme 3, R is allyl, Rp is benzoyl)

To a 0° C. solution in pyridine (20 mL) under $N_2$ of the compound prepared according to Step 8f (10.0 g, 13.9 mmol) was added methanesulfonyl anhydride (4.82 g, 27.7 mmol), and the mixture was stirred at room temperature for 4.5 hours. The mixture was diluted with ethyl acetate and quenched with 5% $KH_2PO_4$. The mixture was washed with water and brine, dried over sodium sulfate, and concentrated in vacuo. The residue was dissolved in acetone (50 mL), and DBU (2.3 mL) was added. The mixture was stirred under nitrogen for 64 hours, then extracted with dichloromethane. The organic phase was washed with brine, dried over sodium sulfate, and concentrated in vacuo. Chromatography on silica gel (30% acetone-hexanes) gave the title compound (8.1 g). MS m/e 700 $(M+H)^+$.

Example 9

Compound of Formula (I): $R^1$ 3-(3-quinolinyl) allyloxy; $R^2$ is H, $R^3$ is Absent, the Double Bond is Present, A, B, D and E are H, and Y and Z Taken Together with the Atom to which they are Attached Form an Oxo Group Treating the compound of Example 8 with palladium(II) acetate, tri-o-tolylphosphine and 3-bromoquinoline in acetonitrile under the conditons of the Heck reaction, the title compound is prepared.

Example 10

Compound of Formula (I): $R^1$ is allyloxy; $R^2$ is H, $R^3$ is Absent, the Double Bond is Present, A, B, D and E are H, Y is H, and Z is cladinose Treating the compound of Example 8 Step c (6-O-allyl erythromycin A, Compound (6) of Scheme 1, R is allyl) with benzoic anhydride to form the 2',4"-di-O-benzoyl compound, then treating this protected compound according to the procedures of Example 1, Steps d and e, then treating the resulting compound with 2-nitroaniline according to the procedure of Example 5 Step a, then deprotecting with methanol and treating the resulting compound with $H_2$ and Pd/C in 10% acetic acid/ethanol, the title compound is prepared.

Example 11

Compound of Formula (I): $R^1$ is 3-(3-quinolinyl) allyloxy; $R^2$ is H, $R^3$ is Absent, the Double Bond is Present, A, B, D and E are H, Y is H, and Z is cladinose Treating the compound of Example 8 Step 8c (6-O-allyl erythromycin A, Compound (6) of Scheme 1, R is allyl) with benzoic anhydride to form the 2',4"-di-O-benzoyl compound, then treating this protected compound with palladium(II)acetate, tri-o-tolylphosphine and 3-bromoquinoline in acetonitrile under the conditons of the Heck reaction, then reacting that product according to the procedures of Example 1, Steps d and e, then treating the resulting compound with 2-nitroaniline according to the procedure of Example 5 Step a, then deprotecting with methanol and treating the resulting compound with $H_2$ and Pd/C in 10% acetic acid/ethanol, the title compound is prepared.

Examples 12–20

Following the procedures of Example 5, except substituting the starting material compounds shown for the 4-methoxy-2-nitroaniline of Example 5, the compounds of Examples 12–20 are prepared as shown in Table 1.

TABLE 1

Examples 12–20

| Ex. No | Starting material | Product |
|---|---|---|
| 12 | 3-amino-4-nitropyridine | Compound of Formula (III): $R^1$ is methoxy; $R^2$ is H, $R^3$ is absent, the double bond is present, A, D, and E are H, and Y and Z taken together with the atom to which they are attached form an oxo group |
| 13 | 4-amino-3-nitropyridine | Compound of Formula (IV): $R^1$ is methoxy; $R^2$ is H, $R^3$ is absent, the double bond is present, A, B, and E are H, and Y and Z taken together with the atom to which they are attached form an oxo group |
| 14 | 3-amino-2-nitropyridine | Compound of Formula (V): $R^1$ is methoxy; $R^2$ is H, $R^3$ is absent, the double bond is present, A, B, and D are H, and Y and Z taken together with the atom to which they are attached form an oxo group |
| 15 | 2-amino-3-nitropyrazine | Compound of Formula (VI): $R^1$ is methoxy; $R^2$ is H, $R^3$ is absent, the double bond is present, B and D are H, and Y and Z taken together with the atom to which they are attached form an oxo group |
| 16 | 4-amino-5-nitropyrimidine | Compound of Formula (VII): $R^1$ is methoxy; $R^2$ is H, $R^3$ is absent, the double bond is present, B and E are H, and Y and Z taken together with the atom to which they are attached form an oxo group |
| 17 | 5-amino-4-nitropyrimidine | Compound of Formula (VIII): $R^1$ is methoxy; $R^2$ is H, $R^3$ is absent, the double bond is present, A and D are H, and Y and Z taken together with the atom to which they are attached form an oxo group |
| 18 | 3-amino-4 nitropyridazine | Compound of Formula (IX): $R^1$ is methoxy; $R^2$ is H, $R^3$ is absent, the double bond is present, D and E are H, and Y and Z taken together with the atom to which they are attached form an oxo group |
| 19 | 4-amino-5-nitropyridazine | Compound of Formula (X): $R^1$ is methoxy; $R^2$ is H, $R^3$ is absent, the double bond is present, A and E are H, and Y and Z taken together with the atom to which they are attached form an oxo group |
| 20 | 4-amino-3-nitropyridazine | Compound of Formula (XI): $R^1$ is methoxy; $R^2$ is H, $R^3$ is absent, the double bond is present, A and B are H, and Y and Z taken together with the atom to which they are attached form an oxo group |

TABLE 2

NMR data for benzodiazepine examples

Chemical shift

| Atom No | Example 2 | | Example 3 | | Example 4 | | Example 5 | | Example 6 | | Example 7 | | Example 8 | |
|---|---|---|---|---|---|---|---|---|---|---|---|---|---|---|
| | 13C—NMR | 1H—NMR | 13C—NMR | 1H—NMR | 13C—NMR | 1H—NMR | 13C—NMR | 1H—NMR | 13C—NMR | 1H—NMR | 13C—NMR | 1H—NMR | 13C—NMR | 1H—NMR |
| 1 | 169.9 | | 169.3 | | 168.9 | | 169.0 | | 168.9 | | 168.8 | | 168.8 | |
| 2 | 51.1 | 3.78 | 51.0 | 3.73 | 51.2 | 3.79 | 51.2 | 3.79 | 51.0 | 3.76 | 51.2 | 3.79 | 51.1 | 3.89 |
| 2-Me | 16.7 | 1.35 | 13.1 | 1.27 | 16.8 | 1.35 | 16.7 | 1.35 | 16.5 | 1.30 | 16.5 | 1.35 | 14.8 | 1.32 |
| 3 | 203.4 | | 202.8 | | 203.5 | | 203.5 | | 203.1 | | 203.6 | | 204.8 | |
| 4 | 48.5 | 3.04 | 45.9 | 3.08 | 48.5 | 3.04 | 48.5 | 3.04 | 48.3 | 2.98 | 48.4 | 3.04 | 37.4 | 3.22 |
| 4-Me | 14.1 | 1.25 | 14.6 | 1.28 | 14.2 | 1.23 | 14.2 | 1.25 | 14.0 | 1.22 | 14.2 | 1.26 | 14.6 | 1.35 |
| 5 | 80.8 | 4.12 | 85.7 | 4.14 | 80.8 | 4.12 | 80.8 | 4.12 | 80.5 | 4.08 | 80.6 | 4.13 | 78.1 | 4.24 |
| 6 | 78.4 | | 78.0 | | 78.4 | | 78.4 | | 78.4 | | 78.5 | | 79.0 | |
| 6-Me | 19.5 | 1.46 | 21.9 | 1.34 | 19.5 | 1.46 | 19.5 | 1.45 | 19.3 | 1.40 | 19.5 | 1.44 | 20.2 | 1.45 |
| O—Me | 49.0 | 2.24 | 50.9 | 2.66 | 49.1 | 2.26 | 49.1 | 2.26 | 48.9 | 2.20 | 49.2 | 2.24 | 39.0 | 1.67, 1.58 |
| 7 | 39.4 | 1.81, 1.48 | 36.3 | 1.48, 1.27 | 39.5 | 1.81, 1.48 | 39.6 | 1.81, 1.48 | 39.4 | 1.80, 1.44 | 39.6 | 1.83, 1.51 | 47.1 | 3.01 |

TABLE 2-continued

NMR data for benzodiazepine examples

Chemical shift

| Atom No | Example 2 13C—NMR | Example 2 1H—NMR | Example 3 13C—NMR | Example 3 1H—NMR | Example 4 13C—NMR | Example 4 1H—NMR | Example 5 13C—NMR | Example 5 1H—NMR | Example 6 13C—NMR | Example 6 1H—NMR | Example 7 13C—NMR | Example 7 1H—NMR | Example 8 13C—NMR | Example 8 1H—NMR |
|---|---|---|---|---|---|---|---|---|---|---|---|---|---|---|
| 8 | 42.4 | 2.97 | 27.7 | 1.66 | 42.5 | 2.96 | 42.6 | 2.96 | 42.3 | 2.93 | 42.7 | 2.98 | 20.0 | 1.24 |
| 8-Me | 19.4 | 1.23 | 20.5 | 1.06 | 19.4 | 1.22 | 19.4 | 1.23 | 19.2 | 1.18 | 19.4 | 1.24 | 175.8 | |
| 9 | 176.0 | | 64.6 | 2.56 | 176.0 | | 176.8 | | 179.3 | | 178.7 | | 42.6 | 3.25 |
| 10 | 37.7 | 3.18 | 33.8 | 2.53 | 37.6 | 3.16 | 37.7 | 3.16 | 38.0 | 3.19 | 37.8 | 3.23 | 11.7 | 0.85 |
| 10-Me | 11.6 | 0.87 | 13.7 | 1.26 | 11.6 | 0.85 | 11.7 | 0.87 | 11.5 | 0.79 | 12.1 | 0.91 | 57.5 | 3.72 |
| 11 | 57.7 | 3.50 | 60.4 | 3.76 | 57.8 | 3.49 | 57.6 | 3.48 | 57.8 | 3.46 | 57.0 | 3.50 | 81.1 | |
| 12 | 80.9 | | 81.9 | | 80.8 | | 80.9 | | 81.4 | | 80.9 | | 14.4 | 1.63 |
| 12-Me | 14.0 | 1.60 | 13.7 | 1.63 | 14.1 | 1.59 | 14.1 | 1.59 | 13.9 | 1.58 | 14.2 | 1.62 | 77.8 | 4.91 |
| 13 | 77.0 | 5.03 | 77.7 | 5.16 | 77.1 | 5.03 | 77.0 | 5.03 | 76.7 | 4.95 | 77.2 | 5.15 | 23.0 | 2.06, 1.65 |
| 14 | 22.4 | 2.03, 1.63 | 22.9 | 2.08, 1.63 | 22.5 | 2.03, 1.63 | 22.5 | 2.03, 1.63 | 22.3 | 1.96, 1.60 | 22.4 | 2.03, 1.62 | 10.8 | 0.98 |
| 15 | 10.3 | 0.91 | 10.8 | 0.98 | 10.4 | 0.91 | 10.4 | 0.91 | 10.2 | 0.86 | 10.2 | 0.89 | 103.4 | 4.29 |
| 1' | 104.1 | 4.26 | 104.6 | 4.24 | 104.1 | 4.26 | 104.1 | 4.26 | 104.0 | 4.21 | 104.1 | 4.26 | 70.3 | 3.20 |
| 2' | 70.3 | 3.22 | 70.1 | 3.19 | 70.4 | 3.21 | 70.4 | 3.22 | 70.2 | 3.16 | 70.4 | 3.22 | 65.9 | 2.45 |
| 3' | 65.8 | 2.55 | 65.7 | 2.46 | 65.9 | 2.44 | 66.0 | 2.47 | 65.7 | 2.40 | 66.0 | 2.47 | 40.2 | 2.27 |
| NMe2 | 40.2 | 2.28 | 40.1 | 2.28 | 40.2 | 2.27 | 40.3 | 2.29 | 40.1 | 2.22 | 40.3 | 2.29 | 28.2 | 1.66, 1.23 |
| 4' | 28.1 | 1.67, 1.24 | 28.0 | 1.69, 1.25 | 28.1 | 1.66, 1.22 | 28.3 | 1.68, 1.24 | 28.0 | 1.63, 1.19 | 28.3 | 1.68, 1.24 | 69.4 | 3.55 |
| 5' | 69.5 | 3.52 | 69.4 | 3.52 | 69.5 | 3.51 | 69.5 | 3.51 | 69.4 | 3.48 | 69.5 | 3.51 | 21.1 | 1.23 |
| 6' | 21.1 | 1.26 | 21.0 | 1.23 | 21.1 | 1.25 | 21.1 | 1.23 | 21.0 | 1.19 | 21.1 | 1.25 | 155.3 | |
| C=O | 155.1 | | 155.7 | | 155.2 | | 155.3 | | 154.5 | | 153.6 | | 135.6 | 7.95 |
| | 135.1 | 8.02 | 141.6 | 7.30 | 134.8 | 7.90 | 156.4 | 7.91 | 138.7 | 8.13 | 146.2 | 8.43 | 134.8 | 7.52 |
| | 134.6 | 7.55 | 127.7 | 7.07 | 134.7 | 7.36 | 136.3 | 7.06 | 135.3 | 7.85 | 142.8 | 7.90 | 134.6 | 7.22 |
| | 129.3 | 7.24 | 127.5 | 6.90 | 134.4 | 7.06 | 124.2 | 6.85 | 133.4 | 7.44 | 141.7 | 7.19 | 129.7 | 7.16 |
| | 126.6 | 7.16 | 126.7 | 6.70 | 127.6 | 2.32 | 122.8 | 3.82 | 129.0 | | 130.7 | | 126.3 | 5.05 |
| | 124.8 | | 121.2 | 4.01 | 126.8 | | 117.9 | | 123.9 | | 120.8 | | 124.7 | 4.26 |
| | 123.1 | | 120.6 | | 122.9 | | 113.6 | | 118.2 | | | | 123.3 | 4.20 |
| | | | | | 20.4 | | 55.5 | | 108.1 | | | | 117.3 | 3.31 |
| | | | | | | | | | | | | | 64.6 | 3.25 |

Biological Data

Example 21

In Vitro Assay of Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay with selected compounds, shown in Table 3 below, demonstrate the antibacterial activity of the compounds of the invention.

TABLE 3

Antibacterial Activity (MIC's) of Selected Compounds

| MICROORGANISM | Ery A (Ref. std) | Cmpd of Ex 2 | Cmpd of Ex 3 | Cmpd of Ex 4 | Cmpd of Ex 5 | Cmpd of Ex 6 | Cmpd of Ex 7 | Cmpd of Ex 8 |
|---|---|---|---|---|---|---|---|---|
| STAPHYLOCOCCUS AUREUS ATCC 6538P | 0.2 | 0.39 | 25 | 0.78 | 0.78 | 0.39 | 0.39 | 0.78 |
| STAPHYLOCOCCUS AUREUS A5177 | 3.1 | 0.39 | 25 | 0.78 | 0.78 | | 0.39 | 0.78 |
| STAPHYLOCOCCUS AUREUS A-5278 | >100 | >100 | >100 | >100 | >100 | >100 | >100 | >100 |
| STAPHYLOCOCCUS AUREUS CMX 642A | 0.39 | 0.39 | 50 | 0.78 | 0.78 | 0.39 | 0.39 | 0.78 |
| STAPHYLOCOCCUS AUREUS NCTC10649M | 0.39 | 0.39 | 50 | 0.78 | 0.78 | 0.39 | 0.39 | 0.78 |
| STAPHYLOCOCCUS AUREUS CMX 553 | 0.39 | 0.39 | 50 | | 0.78 | 0.39 | 0.39 | 0.78 |
| STAPHYLOCOCCUS AUREUS 1775 | >100 | >100 | >100 | | >100 | >100 | >100 | >100 |

TABLE 3-continued

Antibacterial Activity (MIC's) of Selected Compounds

| MICROORGANISM | Ery A (Ref. std) | Cmpd of Ex 2 | Cmpd of Ex 3 | Cmpd of Ex 4 | Cmpd of Ex 5 | Cmpd of Ex 6 | Cmpd of Ex 7 | Cmpd of Ex 8 |
|---|---|---|---|---|---|---|---|---|
| STAPHYLOCOCCUS EPIDERMIDIS 3519 | 0.2 | 0.39 | 50 | | 0.78 | 0.2 | 0.39 | 1.56 |
| ENTEROCOCCUS FAECIUM ATCC 8043 | 0.1 | 0.2 | 12.5 | | 0.1 | 0.05 | 0.1 | 0.78 |
| STREPTOCOCCUS BOVIS A-5169 | 0.01 | 0.1 | 1.56 | 0.01 | 0.02 | 0.01 | 0.05 | 0.1 |
| STREPTOCOCCUS AGALACTIAE CMX 508 | 0.02 | 0.1 | 3.1 | 0.01 | 0.02 | 0.05 | 0.05 | 0.39 |
| STREPTOCOCCUS PYOGENES EES61 | 0.02 | 0.1 | 3.1 | 0.01 | 0.02 | 0.01 | 0.05 | 0.39 |
| STREPTOCOCCUS PYOGENES 930 | >100 | >100 | >100 | >100 | >100 | >100 | >100 | >100 |
| STREPTOCOCCUS PYOGENES PIU 2548 | 3.1 | 0.39 | 25 | 0.2 | 0.39 | 0.39 | 0.39 | 0.78 |
| MICROCOCCUS LUTEUS ATCC 9341 | 0.02 | 0.1 | 3.1 | 0.1 | 0.1 | 0.05 | 0.05 | 0.78 |
| MICROCOCCUS LUTEUS ATCC 4698 | 0.39 | 0.78 | 25 | 0.2 | 0.78 | 0.39 | 0.39 | 1.56 |
| ESCHERICHA COLI SS | 0.39 | 1.56 | 100 | 0.2 | 50 | 3.1 | 0.78 | 12.5 |
| ESCHERICHIA COLI JUHL | 50 | >100 | >100 | >100 | >100 | >100 | >100 | >100 |
| ESCHERICHIA COLI DC-2 | 100 | >100 | >100 | >100 | >100 | >100 | >100 | >100 |
| CANDIDA ALBICANS CCH 442 | >100 | >100 | >100 | >100 | >100 | >100 | >100 | >100 |
| MYCOBACTERIUM SMEGMATIS ATCC 114 | 1.56 | 3.1 | 50 | 100 | 1.56 | 0.1 | 3.1 | 6.2 |
| N. ASTEROIDES ATCC 9970 | 0.1 | 0.39 | 6.2 | 0.1 | 0.2 | 0.39 | 0.1 | 3.1 |

What is claimed is:

1. A compound selected from the group consisting of:

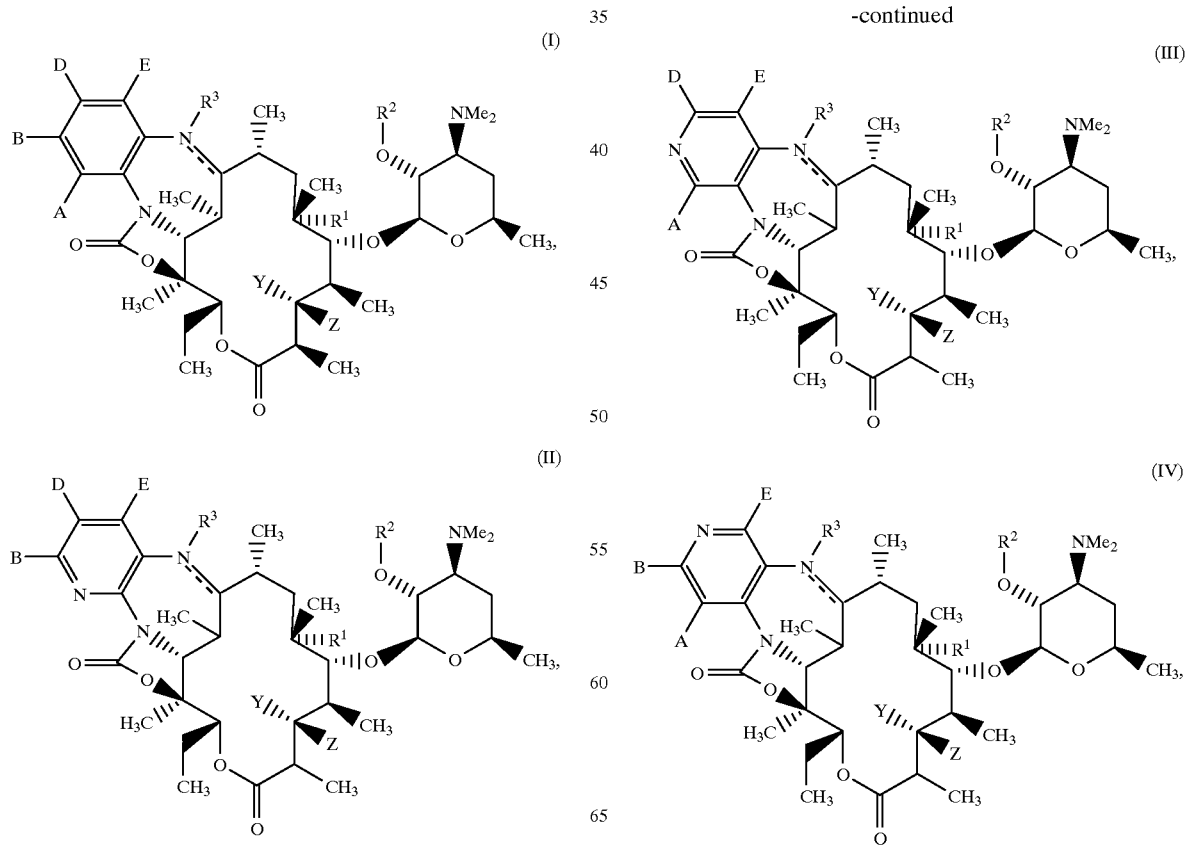

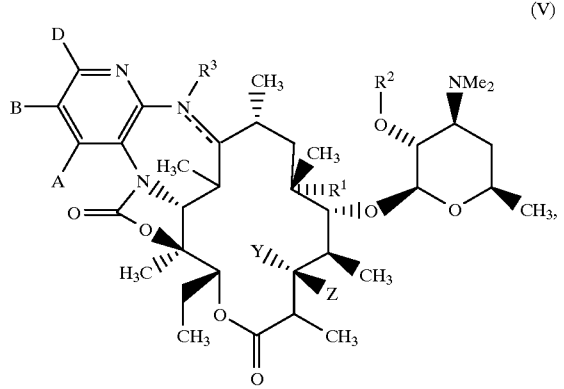
(V)
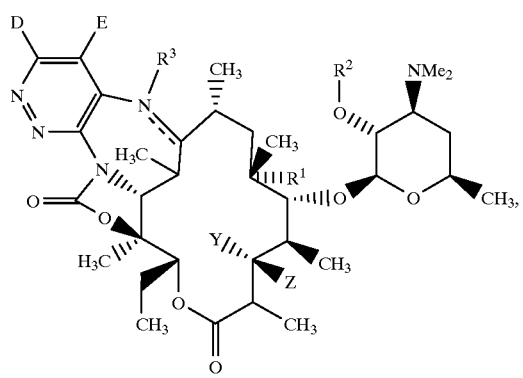
(IX)
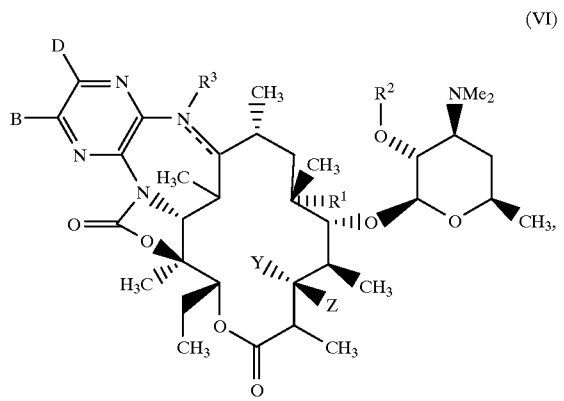
(VI)
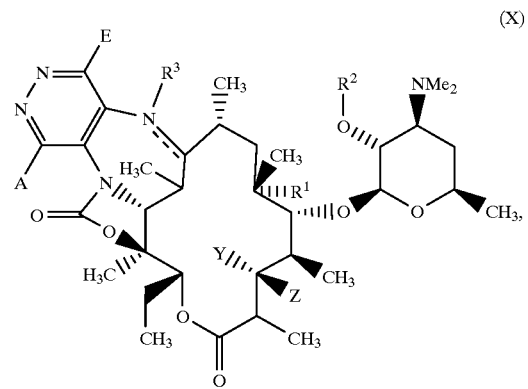
(X)
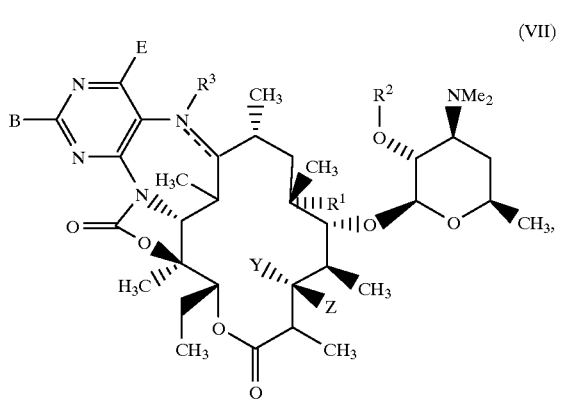
(VII)
and
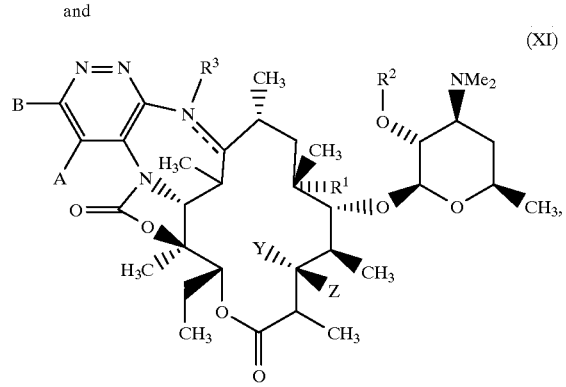
(XI)
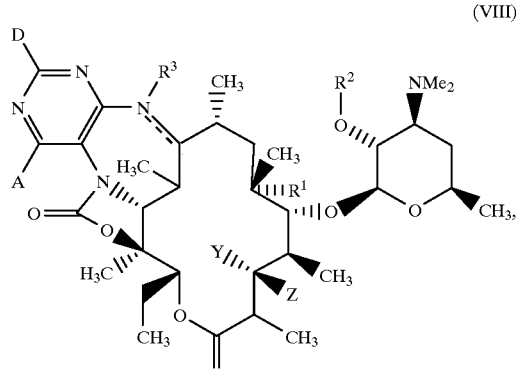
(VIII)
wherein
each of A, B, D and E is independently a group having the formula —(CH$_2$)$_m$—M—(CH$_2$)$_n$—X, wherein
  m is 0, 1, 2 or 3;
  n is 0, 1, 2 or 3;
  M is absent or is selected from the group consisting of:
  (i) —O—;
  (ii) —NH—;
  (iii) —NR$^4$—, wherein R$^4$ is C$_1$–C$_6$-alkyl optionally substituted with halogen, aryl or heteroaryl;
  (iv) —S(O)$_q$—, wherein q is 0, 1 or 2;
  (v) —C(O)—;
  (vi) —C(O)—NH—;
  (vii) —NH—C(O)—;
  (viii) —C(O)—O—
  (ix) —O—C(O)—;

(x) —CH=CH—;
(xi) —C≡C—; and

X is selected from the group consisting of:
(i) H;
(ii) CN;
(iii) halogen;
(iv) $NO_2$;
(v) aryl;
(vi) substituted-aryl;
(vii) heteroaryl;
(viii) substituted-heteroaryl;
(ix) heterocycloalkyl; and
(x) $C_3$–$C_7$-cycloalkyl;
(xi) $C_1$–$C_6$-alkyl;
(xii) $C_1$–$C_6$-acyl; or
one pair of A, B, D and E, selected from the group consisting of A&B, B&D, and D&E, may, when such combinations are possible, additionally combine with the atoms to which they are attached to form a ring selected from the group consisting of benzene, pyridine, pyridazine, pyrimidine, pyrazine, pryazole, imidazole, triazole, pyrrole, furan, thiophene, oxazole, 1,3-dioxocyclopent-2-ene and 1,4-dioxocyclohex-2-ene;

$R^1$ is selected from the group consisting of:
(a) hydrogen;
(b) hydroxy;
(c) a protected hydroxy group;
(d) O—R, wherein R is selected from the group consisting of
  (1) methyl substituted with a moiety selected from the group consisting of
    (a) CN,
    (b) F,
    (c) —$C_2R^5$ wherein $R^5$ is $C_1$–$C_3$-alkyl or aryl substituted $C_1$–$C_3$-alkyl, or heteroaryl substituted $C_1$–$C_3$-alkyl,
    (d) $S(O)_nR^5$ where n is 0, 1 or 2 and $R^5$ is as defined above,
    (e) $C(O)NHR^5$ where $R^5$ is as defined above,
    (f) $C(O)NR^6R^7$ wherein $R^6$ and $R^7$ are independently selected from hydrogen and $C_1$–$C_3$-alkyl,
    (g) aryl,
    (h) substituted aryl,
    (i) heteroaryl, and
    (j) substituted heteroaryl,
  (2) $C_2$–$C_{10}$-alkyl,
  (3) $C_2$–$C_{10}$-alkyl substituted with one or more substituents selected from the group consisting of
    (a) halogen,
    (b) hydroxy,
    (c) $C_1$–$C_3$-alkoxy,
    (d) $C_1$-$C_3$-alkoxy-$C_1$-$C_3$-alkoxy,
    (e) oxo,
    (f) —$N_3$,
    (g) —CHO,
    (h) O—$SO_2$-(substituted $C_1$–$C_6$-alkyl),
    (i) —$NR^8R^9$ wherein $R^8$ and $R^9$ are independently selected from the group consisting of
      (i) hydrogen,
      (ii) $C_1$–$C_{12}$-alkyl,
      (iii) substituted $C_1$–$C_{12}$-alkyl,
      (iv) $C_1$–$C_{12}$-alkenyl,
      (v) substituted $C_1$–$C_{12}$-alkenyl,
      (vi) $C_1$–$C_{12}$-alkynyl,
      (vii) substituted $C_1$–$C_{12}$-alkynyl,
      (viii) aryl,
      (ix) $C_3$–$C_8$-cycloalkyl,
      (x) substituted $C_3$–$C_8$-cycloalkyl,
      (xi) substituted aryl,
      (xii) heterocycloalkyl,
      (xiii) substituted heterocycloalkyl,
      (xiv) $C_1$–$C_{12}$-alkyl substituted with aryl,
      (xv) $C_1$–$C_{12}$-alkyl substituted with substituted aryl,
      (xvi) $C_1$–$C_{12}$-alkyl substituted with heterocycloalkyl,
      (xvii) $C_1$–$C_{12}$-akl substituted with substituted heterocycloalkyl,
      (xviii) $C_1$–$C_{12}$-alkyl substituted with $C_3$–$C_8$-cycloalkyl,
      (xix) $C_1$–$C_{12}$-alkyl substituted with substituted $C_3$–$C_8$-cycloalkyl,
      (xx) heteroaryl,
      (xxi) substituted heteroaryl,
      (xxii) $C_1$–$C_{12}$-alkyl substituted with heteroaryl, and
      (xxiii) $C_1$–$C_{12}$-alkyl substituted with substituted heteroaryl,
      or $R^8$ and $R^9$ are taken together with the atom to which they are attached form a 3–10 membered heterocycloalkyl ring which may be substituted with one or more substituents independently selected from the group consisting of:
        (i) halogen,
        (ii) hydroxy,
        (iii) $C_1$–$C_3$-alkoxy,
        (iv) $C_1$–$C_3$-alkoxy-$C_1$–$C_3$-alkoxy,
        (v) oxo,
        (vi) $C_1$–$C_3$-alkyl,
        (vii) halo-$C_1$–$C_3$-alkyl, and
        (viii) $C_1$–$C_3$-alkoxy-$C_1$–$C_3$-alkyl,
    (j) —$CO_2R^5$ wherein $R^5$ is as defined above,
    (k) —$C(O)NR^6R^7$ wherein $R^6$ and $R^7$ are as defined above,
    (l) =N—O—$R^5$ wherein $R^6$ is as previously defined,
    (m) —C≡N,
    (n) O—$S(O)_nR^5$ wherein n is 0, 1 or 2 and $R^5$ is as defined above,
    (o) aryl,
    (p) substituted aryl,
    (q) heteroaryl,
    (r) substituted heteroaryl,
    (s) $C_3$–$C_8$-cycloalkyl,
    (t) substituted $C_3$–$C_8$-cycloalkyl,
    (u) $C_1$–$C_{12}$-alkyl substituted with heteroaryl,
    (v) heterocycloalkyl,
    (w) substituted heterocycloalkyl,
    (x) $NHC(O)R^5$ where $R^5$ is as previously defined,
    (y) $NHC(O)NR^6R^7$ wherein $R^6$ and $R^7$ are as previously defined,
    (z) =N—$NR^8R^9$ wherein $R^8$ and $R^9$ are as previously defined,
    (aa) =N—$R^{11}$ wherein $R^{11}$ is as previously defined,
    (bb) =N—$NHC(O)R^5$ wherein $R^5$ is as previously defined, and
    (cc) =N—$NHC(O)NR^6R^7$ wherein $R^6$ and $R^7$ are as previously defined;
  (4) $C_3$-alkenyl substituted with a moiety selected from the group consisting of
    (a) halogen,
    (b) —CHO, (c) —CO$_2$R$^5$ where R$^5$ is as defined above,
(d) —C(O)—R$^{11}$ where R$^{11}$ is as defined above,
(e) —C(O)NR$^6$R$^7$ wherein R$^6$ and R$^7$ are as previously defined,
(f) —C≡N,
(g) aryl,
(h) substituted aryl,
(i) heteroaryl,
(j) substituted heteroaryl,
(k) C$_3$–C$_7$-cycloalkyl, and
(l) C$_1$–C$_{12}$-alkyl substituted with heteroaryl,
(5) C$_4$–C$_{10}$-alkenyl,
(6) C$_4$–C$_{10}$-alkenyl substituted with one or more substituents selected from the group consisting of
    (a) halogen,
    (b) C$_1$–C$_3$-alkoxy,
    (c) oxo,
    (d) —CHO,
    (e) —CO$_2$R$^5$ where R$^5$ is as defined above,
    (f) —C(O)NR$^6$R$^7$ wherein R$^6$ and R$^7$ are as previously defined,
    (g) —NR$^8$R$^9$ wherein R$^8$ and R$^9$ are as previously defined,
    (h) =N—O—R$^5$ where R$^5$ is as previously defined,
    (i) —C≡N,
    (j) O—S(O)$_n$R$^5$ where n is 0, 1 or 2 and R$^5$ is as previously defined,
    (k) aryl,
    (l) substituted aryl,
    (m) heteroaryl,
    (n) substituted heteroaryl,
    (o) C$_3$–C$_7$-cycloalkyl,
    (p) C$_1$–C$_{12}$-alkyl substituted with heteroaryl,
    (q) NHC(O)R$^5$ where R$^5$ is as previously defined,
    (r) NHC(O)NR$^6$R$^7$ wherein R$^6$ and R$^7$ are as previously defined,
    (s) =N—NR$^8$R$^9$ wherein R$^8$ and R$^9$ are as previously defined,
    (t) =N—R$^{11}$ wherein R$^{11}$ is as previously defined,
    (u) =N—NHC(O)R$^5$ where R$^5$ is as previously defined, and
    (v) =N—NHC(O)NR$^6$R$^7$ wherein R$^6$ and R$^7$ are as previously defined;
(7) C$_3$–C$_{10}$-alkynyl; and
(8) C$_3$–C$_{10}$-alkynyl substituted with one or more substituents selected from the group consisting of
    (a) trialkylsilyl,
    (b) aryl,
    (c) substituted aryl,
    (d) heteroaryl, and
    (e) substituted heteroaryl;
R$^2$ is hydrogen or a hydroxy protecting group;
the dashed line represents an optional double bond;
R$^3$ is absent or oxygen when the optional double bond is persent;
R$^3$ is selected from the group consisting of hydrogen, C$_1$–C$_6$ acyl and C$_1$–C$_6$ alkyl optionally substituted with halogen, aryl or heteroaryl, when the optional double bond is absent; and
Y and Z are both hydrogen, or one of Y and Z is hydrogen and the other is selected from the group consisting of hydroxy, protected hydroxy, and cladinosyl, or Y and Z are taken together with the atom to which they are attached to form an oxo group.

2. A compound according to claim 1 having the formula (I)

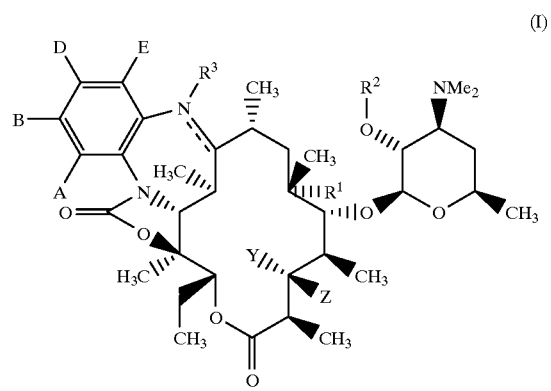

3. A compound according to claim 2 wherein Y and Z are taken together with the atom to which they are attached to form an oxo group.

4. A compound according to claim 3 which is selected from the group consisting of:
compound of Formula (I): R$^1$ is methoxy; R$^2$ is H, R$^3$ is H, the double bond is absent, A, B, D and E are H, and Y and Z taken together with the atom to which they are attached form an oxo group;
compound of Formula (I): R$^1$ is methoxy; R$^2$ is H, R$^3$ is absent, the double bond is present, A, B, and E are H, D is methyl, and Y and Z taken together with the atom to which they are attached form an oxo group;
compound of Formula (I): R$^1$ is methoxy; R$^2$ is H, R$^3$ is absent, the double bond is present, A, B, and E are H, D is methoxy, and Y and Z taken together with the atom to which they are attached form an oxo group;
compound of Formula (I): R$^1$ is methoxy; R$^2$ is H, R$^3$ is absent, the double bond is present, A, B, and E are H, D is cyano, and Y and Z taken together with the atom to which they are attached form an oxo group;
compound of Formula (I): R$^1$ is methoxy; R$^2$ is H, R$^3$ is H, the double bond is absent, B, D, and E are H, and Y and Z taken together with the atom to which they are attached form an oxo group;
compound of Formula (I): R$^1$ is allyloxy; R$^2$ is H, R$^3$ is H, the double bond is absent, A, B, D and E are H, and Y and Z taken together with the atom to which they are attached form an oxo group;
compound of Formula (I): R$^1$ 3-(3-quinolinyl)allyloxy; R$^2$ is H, R$^3$ is absent, the double bond is present, A, B, D and E are H, and Y and Z taken together with the atom to which they are attached form an oxo group;
compound of Formula (I): R$^1$ is allyloxy; R$^2$ is H, R$^3$ is absent, the double bond is present, A, B, D and E are H, Y is H, and Z is cladinosyl; and
compound of Formula (I): R$^1$ is 3-(3-quinolinyl)allyloxy; R$^2$ is H, R$^3$ is absent, the double bond is present, A, B, D and E are H, Y is H, and Z is cladinose.

5. A compound according to claim 1 having the formula (II)

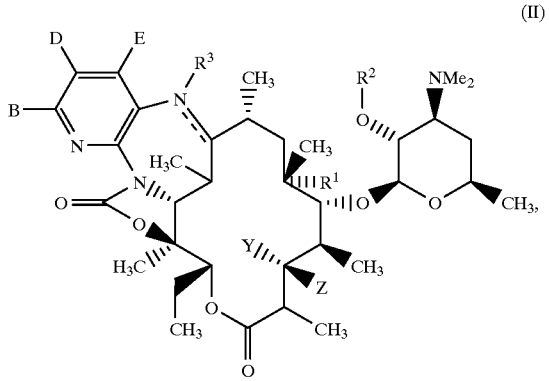

(II)

6. A compound according to claim 5 which is:

compound of Formula (II): $R^1$ is methoxy; $R^2$ is H, $R^3$ is absent, the double bond is present, B, D, and E are H, and Y and Z taken together with the atom to which they are attached form an oxo group.

7. A compound according to claim 1 having the formula (III)

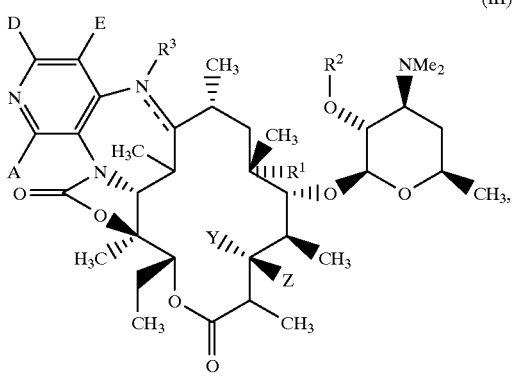

(III)

8. A compound according to claim 7 which is:

compound of Formula (III): $R^1$ is methoxy; $R^2$ is H, $R^3$ is absent, the double bond is present, A, D, and E are H, and Y and Z taken together with the atom to which they are attached form an oxo group.

9. A compound according to claim 1 having the formula (IV)

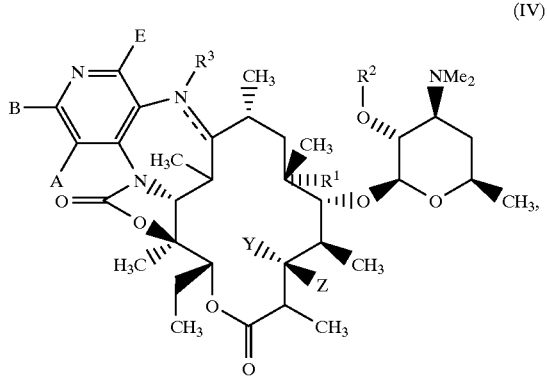

(IV)

10. A compound according to claim 9 which is:

compound of Formula (IV): $R^1$ is methoxy; $R^2$ is H, $R^3$ is absent, the double bond is present, A, B, and E are H, and Y and Z taken together with the atom to which they are attached form an oxo group.

11. A compound according to claim 1 having the formula (V)

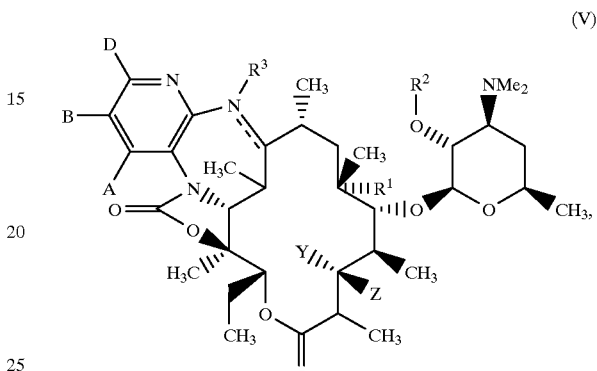

(V)

12. A compound according to claim 11 which is:

compound of Formula (V): $R^1$ is methoxy; $R^2$ is H, $R^3$ is absent, the double bond is present, A, B, and D are H, and Y and Z taken together with the atom to which they are attached form an oxo group.

13. A compound according to claim 1 having the formula (VI)

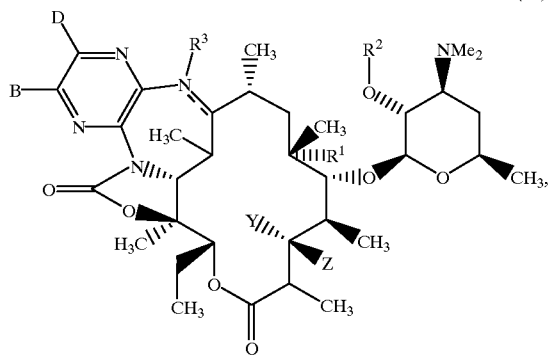

(VI)

14. A compound according to claim 13 which is:

compound of Formula (VI): $R^1$ is methoxy; $R^2$ is H, $R^3$ is absent, the double bond is present, B and D are H, and Y and Z taken together with the atom to which they are attached form an oxo group.

15. A compound according to claim 1 having the formula (VII)

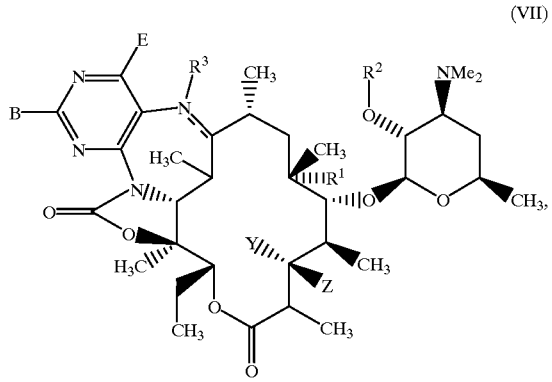
(VII)

16. A compound according to claim 15 which is:
compound of Formula (VII): $R^1$ is methoxy; $R^2$ is H, $R^3$ is absent, the double bond is present, B and E are H, and Y and Z taken together with the atom to which they are attached form an oxo group.

17. A compound according to claim 1 having the formula (VIII)

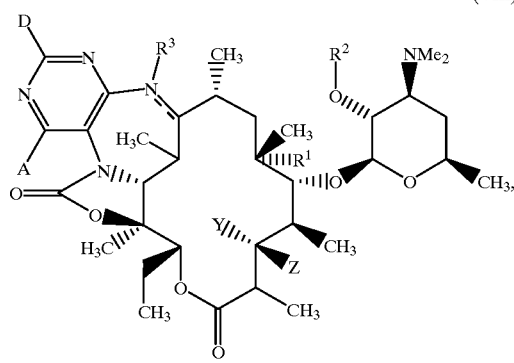
(VIII)

18. A compound according to claim 17 which is:
compound of Formula (VIII): $R^1$ is methoxy; $R^2$ is H, $R^3$ is absent, the double bond is present, A and D are H, and Y and Z taken together with the atom to which they are attached form an oxo group.

19. A compound according to claim 1 having the formula (IX)

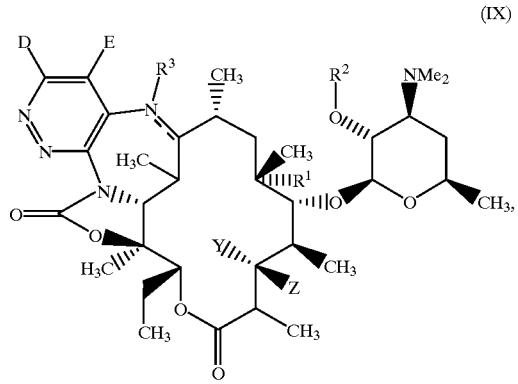
(IX)

20. A compound according to claim 19 which is:
compound of Formula (IX): $R^1$ is methoxy; $R^2$ is H, $R^3$ is absent, the double bond is present, D and E are H, and Y and Z taken together with the atom to which they are attached form an oxo group.

21. A compound according to claim 1 having the formula (X)

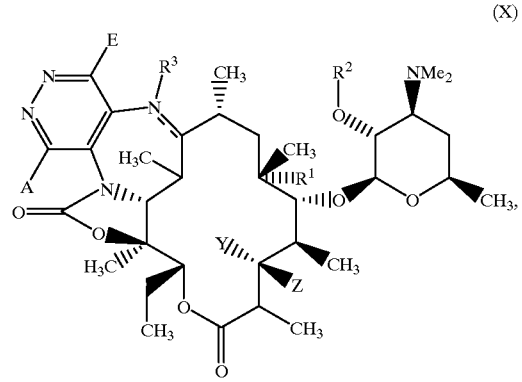
(X)

22. A compound according to claim 21 which is:
compound of Formula (X): $R^1$ is methoxy; $R^2$ is H, $R^3$ is absent, the double bond is present, A and E are H, and Y and Z taken together with the atom to which they are attached form an oxo group.

23. A compound according to claim 1 having the formula (XI)

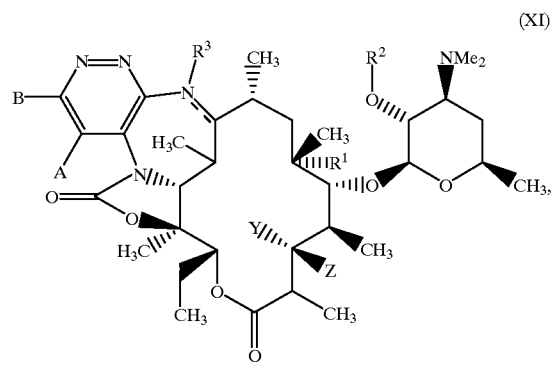
(XI)

24. A compound according to claim 23 which is:
compound of Formula (XI): $R^1$ is methoxy; $R^2$ is H, $R^3$ is absent, the double bond is present, A and B are H, and Y and Z taken together with the atom to which they are attached form an oxo group.

25. A process for preparing a compound having a formula selected from the group consisting of

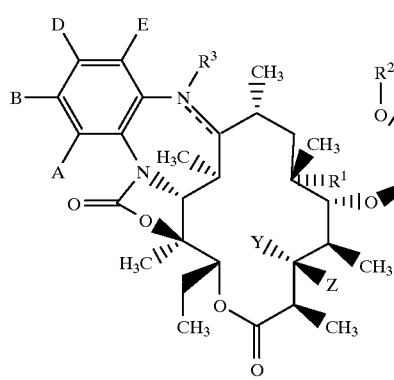 (I)
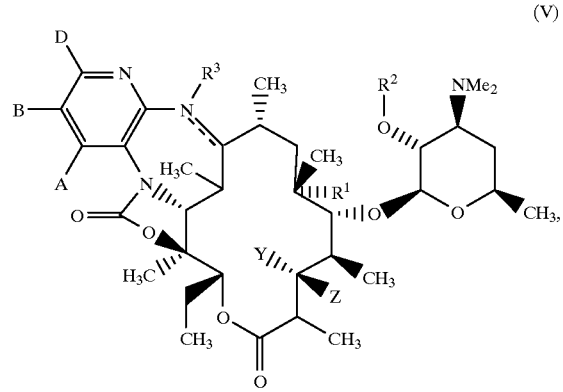 (V)
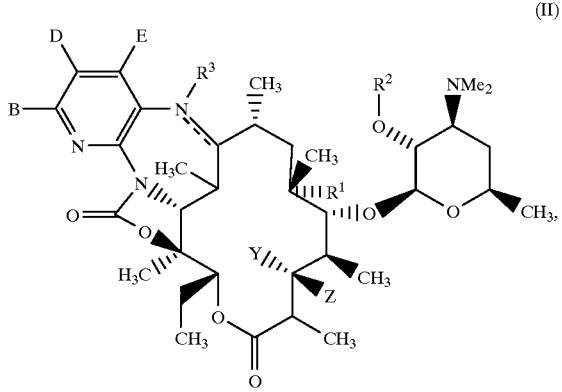 (II)
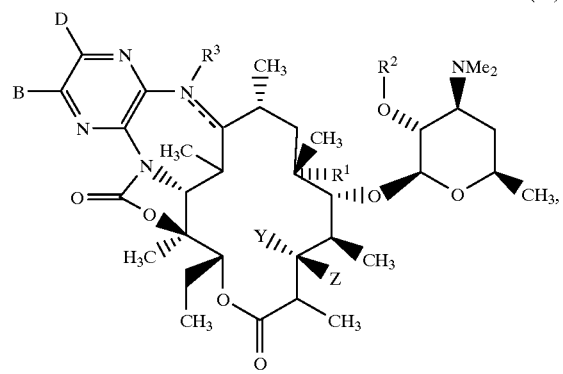 (VI)
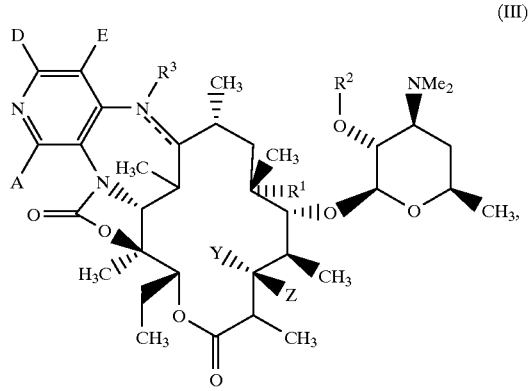 (III)
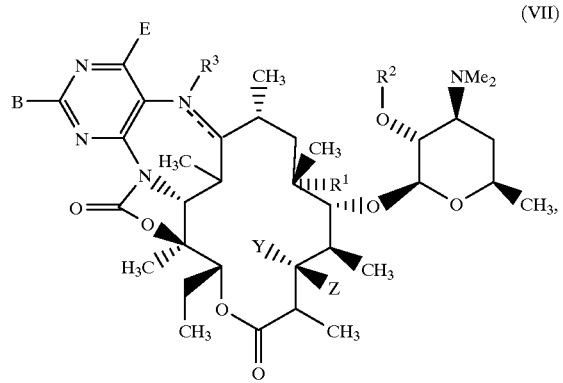 (VII)
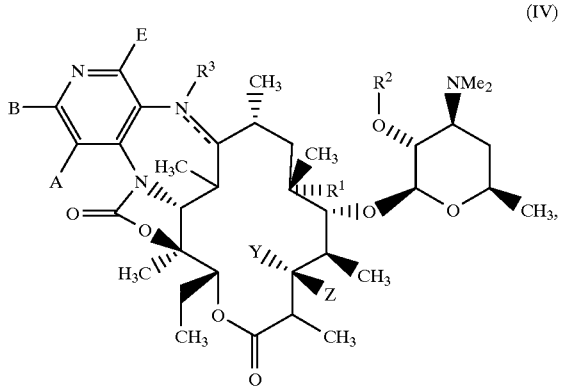 (IV)
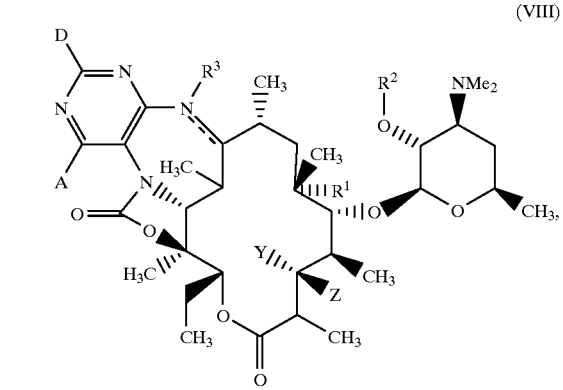 (VIII)

-continued

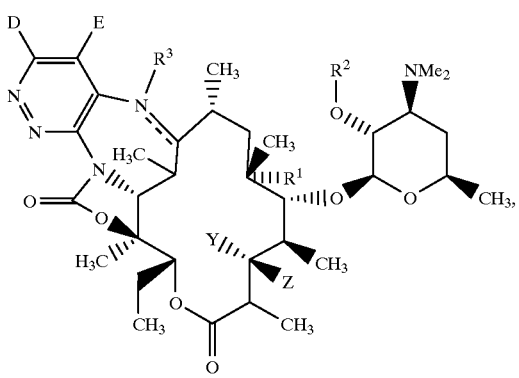

(IX)

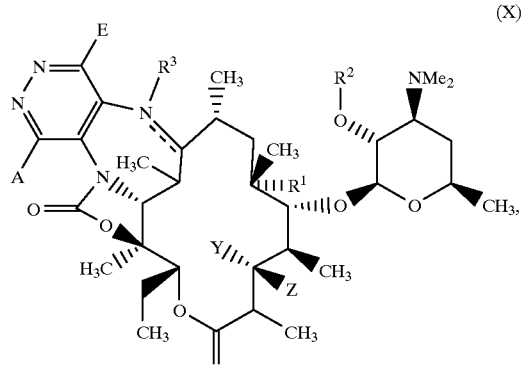

(X)

and

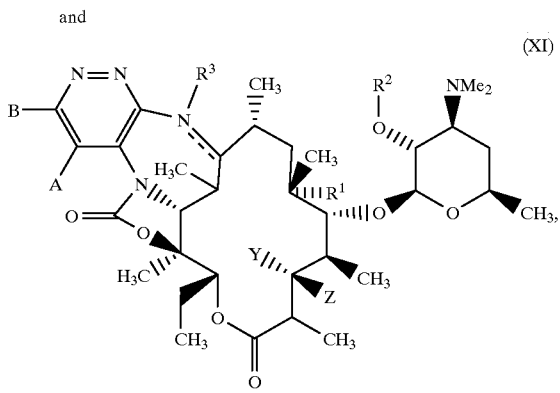

(XI)

wherein
each of A, B, D and E is independently a group having the formula —(CH$_2$)m—M—(CH$_2$)$_n$—X, wherein
m is 0, 1, 2 or 3;
n is 0, 1, 2 or 3;
M is absent or is selected from the group consisting of:
(i) —O—;
(ii) —NH—;
(iii) —NR$^4$—, wherein R$^4$ is C$_1$–C$_6$-alkyl optionally substituted with halogen, aryl or heteroaryl;
(iv) —S(O)$_q$—, wherein q is 0, 1 or 2;
(v) —C(O)—;
(vi) —C(O)—NH—;
(vii) —NH—C(O)—;
(viii) —C(O)—O—
(ix) —O—C(O)—;
(x) —CH=CH—; and
(xi) —C≡C—;

X is selected from the group consisting of:
(i) H;
(ii) CN;
(iii) halogen;
(iv) NO$_2$;
(v) aryl;
(vi) substituted-aryl;
(vii) heteroaryl;
(viii) substituted-heteroaryl;
(ix) heterocycloalkyl; and
(x) C$_3$–C$_7$-cycloalkyl;
(xi) C$_1$–C$_6$-alkyl; and
(xii) C$_1$–C$_6$-acyl; or one pair of A, B, D and E, selected from the group consisting of A&B, B&D, and D&E, may, when such combinations are possible, additionally combine with the atoms to which they are attached to form a ring selected from the group consisting of benzene, pyridine, pyridazine, pyrimidine, pyrazine, pryazole, imidazole, triazole, pyrrole, furan, thiophene, oxazole, 1,3-dioxocyclopent-2-ene and 1,4-dioxocyclohex-2-ene;

R$^1$ is selected from the group consisting of:
(a) hydrogen;
(b) hydroxy;
(c) a protected hydroxy group;
(d) O—R, wherein R is selected from the group consisting of
(1) methyl substituted with a moiety selected from the group consisting of
(a) CN,
(b) F,
(c) —CO$_2$R$^5$ wherein R$^5$ is C$_1$–C$_3$-alkyl or aryl substituted C$_1$–C$_3$-alkyl, or heteroaryl substituted C$_1$–C$_3$-alkyl,
(d) S(O)$_n$R$^5$ where n is 0, 1 or 2 and R$^5$ is as defined above,
(e) NHC(O)R$^5$ where R$^5$ is as defined above,
(f) NHC(O)NR$^6$R$^7$ wherein R$^6$ and R$^7$ are independently selected from hydrogen and C$_1$–C$_3$-alkyl,
(g) aryl,
(h) substituted aryl,
(i) heteroaryl, and
(j) substituted heteroaryl,
(2) C$_2$–C$_{10}$-alkyl,
(3) C$_2$–C$_{10}$-alkyl substituted with one or more substituents selected from the group consisting of
(a) halogen,
(b) hydroxy,
(c) C$_1$–C$_3$-alkoxy,
(d) C$_1$–C$_3$-alkoxy-C$_1$–C$_3$-alkoxy,
(e) oxo,
(f) —N$_3$,
(g) —CHO,
(h) O—SO$_2$-(substituted C$_1$–C$_6$-alkyl), and
(i) —NR$^8$R$^9$ wherein R$^8$ and R$^9$ are independently selected from the group consisting of
(i) hydrogen,
(ii) C$_1$–C$_{12}$-alkyl, (iii) substituted $C_1$–$C_{12}$-alkyl,
(iv) $C_1$–$C_{12}$-alkenyl,
(v) substituted $C_1$–$C_{12}$-alkenyl,
(vi) $C_1$–$C_{12}$-alkynyl,
(vii) substituted $C_1$–$C_{12}$-alkynyl,
(viii) aryl,
(ix) $C_3$–$C_8$-cycloalkyl,
(x) substituted $C_3$–$C_8$-cycloalkyl,
(xi) substituted aryl,
(xii) heterocycloalkyl,
(xiii) substituted heterocycloalkyl,
(xiv) $C_1$–$C_{12}$-alkyl substituted with aryl,
(xv) $C_1$–$C_{12}$-alkyl substituted with substituted aryl,
(xvi) $C_1$–$C_{12}$-alkyl substituted with heterocycloalkyl,
(xvii) $C_1$–$C_{12}$-alkyl substituted with substituted heterocycloalkyl,
(xviii) $C_1$–$C_{12}$-alkyl substituted with $C_3$–$C_8$-cycloalkyl,
(xix) $C_1$–$C_{12}$-alkyl substituted with substituted $C_3$–$C_8$-cycloalkyl,
(xx) heteroaryl,
(xxi) substituted heteroaryl,
(xxii) $C_1$–$C_{12}$-alkyl substituted with heteroaryl, and
(xxiii) $C_1$–$C_{12}$-alkyl substituted with substituted heteroaryl,
or $R_8$ and $R^9$ are taken together with the atom to which they are attached form a 3–10 membered heterocycloalkyl ring which may be substituted with one or more substituents independently selected from the group consisting of:
(i) halogen,
(ii) hydroxy,
(iii) $C_1$–$C_3$-alkoxy,
(iv) $C_1$–$C_3$-alkoxy-$C_1$–$C_3$-alkoxy,
(v) oxo,
(vi) $C_1$–$C_3$-alkyl,
(vii) halo-$C_1$–$C_3$-alkyl, and
(vii) $C_1$–$C_3$-alkoxy-$C_1$–$C_3$-alkyl,
(j) —$CO_2R^5$ wherein $R^5$ is as defined above,
(k) —$C(O)NR^6R^7$ wherein $R^6$ and $R^7$ are as defined above,
(l) =N—O—$R^5$ wherein $R^6$ is as previously defined,
(m) —C≡N,
(n) O—$S(O)_nR^5$ wherein n is 0, 1 or 2 and $R^5$ is as defined above,
(o) aryl,
(p) substituted aryl,
(q) heteroaryl,
(r) substituted heteroaryl,
(s) $C_3$–$C_8$-cycloalkyl,
(t) substituted $C_3$–$C_8$-cycloalkyl,
(u) $C_1$–$C_{12}$-alkyl substituted with heteroaryl,
(v) heterocycloalkyl,
(w) substituted heterocycloalkyl,
(x) $NHC(O)R^5$ where $R^5$ is as previously defined,
(y) $NHC(O)NR^6R^7$ wherein $R^6$ and $R^7$ are as previously defined,
(z) =N—$NR^8R^9$ wherein $R^8$ and $R^9$ are as previously defined,
(aa) =N—$R^{11}$ wherein $R^{11}$ is as previously defined,
(bb) =N—$NHC(O)R^5$ wherein $R^5$ is as previously defined, and
(cc) =N—$NHC(O)NR^6R^7$ wherein $R^6$ and $R^7$ are as previously defined;
(4) $C_3$-alkenyl substituted with a moiety selected from the group consisting of
(a) halogen,
(b) —CHO,
(c) —$CO_2R^5$ where $R^5$ is as defined above,
(d) —C(O)—$R^{11}$ where $R^{11}$ is as defined above,
(e) —$C(O)NR^6R^7$ wherein $R^6$ and $R^7$ are as previously defined,
(f) —C≡N,
(g) aryl,
(h) substituted aryl,
(i) heteroaryl,
(j) substituted heteroaryl,
(k) $C_3$–$C_7$-cycloalkyl, and
(l) $C_1$–$C_{12}$-alkyl substituted with heteroaryl,
(5) $C_4$–$C_{10}$-alkenyl;
(6) $C_4$–$C_{10}$-alkenyl substituted with one or more substituents selected from the group consisting of
(a) halogen,
(b) $C_1$–$C_3$-alkoxy,
(c) oxo,
(d) —CHO,
(e) —$CO_2R^5$ where $R^5$ is as defined above,
(f) —$C(O)NR^6R^7$ wherein $R^6$ and $R^7$ are as previously defined,
(g) —$NR^8R^9$ wherein $R^8$ and $R^9$ are as previously defined,
(h) =N—O—$R^5$ where $R^5$ is as previously defined,
(i) —C≡N,
(j) O—$S(O),R^5$ where n is 0, 1 or 2 and $R^5$ is as previously defined,
(k) aryl,
(l) substituted aryl,
(m) heteroaryl,
(n) substituted heteroaryl,
(o) $C_3$–$C_7$-cycloalkyl,
(p) $C_1$–$C_{12}$-alkyl substituted with heteroaryl,
(q) $NHC(O)R^5$ where $R^5$ is as previously defined,
(r) $NHC(O)NR^6R^7$ wherein $R^6$ and $R^7$ are as previously defined,
(s) =N—$NR^8R^9$ wherein $R^8$ and $R^9$ are as previously defined,
(t) =N—$R^{11}$ wherein $R^{11}$ is as previously defined,
(u) =N—$NHC(O)R^5$ where $R^5$ is as previously defined, and
(v) =N—$NHC(O)NR^6R^7$ wherein $R^6$ and $R^7$ are as previously defined;
(7) $C_3$–$C_{10}$-alkynyl; and
(8) $C_3$–$C_{10}$-alkynyl substituted with one or more substituents selected from the group consisting of
(a) trialkylsilyl,
(b) aryl,
(c) substituted aryl,
(d) heteroaryl, and
(e) substituted heteroaryl;
$R^2$ is hydrogen or a hydroxy protecting group;
the dashed line represents an optional double bond;
$R^3$ is absent or oxygen when the optional double bond is present;
$R^3$ is selected from the group consisting of hydrogen, $C_1$–$C_6$acyl and $C_1$–$C_6$alkyl optionally substituted with halogen, aryl or heteroaryl, when the optional double bond is absent; and Y and Z are both hydrogen, or one of Y and Z is hydrogen and the other is selected from the group consisting of hydroxy, protected hydroxy, and cladinosyl, or Y and Z are taken together with the atom to which they are attached to form an oxo group;

the method comprising (a) treating in an aprotic solvent in the presence of a base a compound having the formula

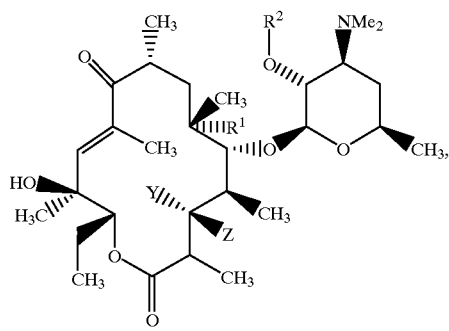

wherein $R^2$ is hydrogen or a hydroxy protecting group; and $R^1$, Y and Z are as defined in claim 1;

with a reagent selected from the group consisting of (1) an isocyanate compound having the formula Nitroaryl—N=C=O, wherein the Nitroaryl moiety is selected from the group consisting of (a)
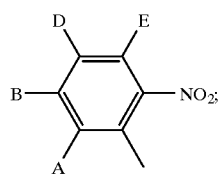

(b)
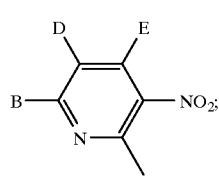

(c)
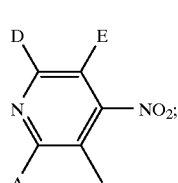

(d)
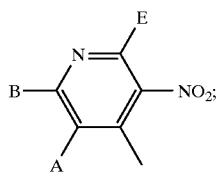

(e)
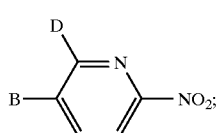

(f)
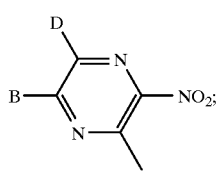

(g)
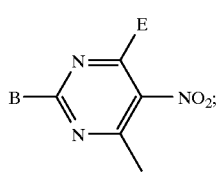

(h)
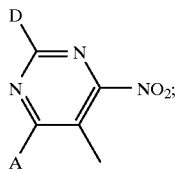

(i)
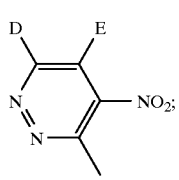

(j)
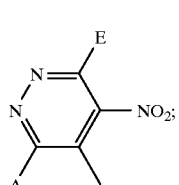

and

-continued

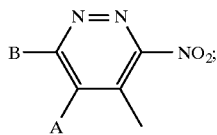

wherein A, B, D and E are as previously defined, and (2) an amine compound having the formula Nitroaryl—NH$_2$, wherein the Nitroaryl moiety is as defined above, in combination with carbonyldiimidazole;

to give a compound having the formula

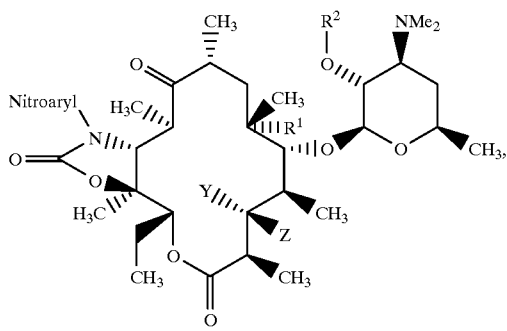

(b) optionally deprotecting;

(c) reducing the nitro group of the Nitroaryl moiety of the compound of step (b) to give a compound having the formula

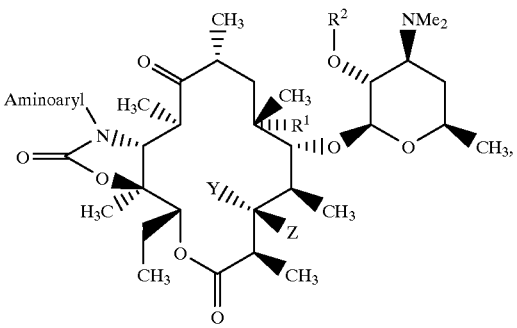

(d) cyclizing the compound of step (c) by treatment with dilute acid to give a compound of a formula (I)–(XI) wherein the optional double bond is present and R$^3$ is absent;

(e) optionally oxidizing the imine nitrogen; optionally reducing the imine; optionally oxidizing the reduced imine nitrogen; optionally derivatizing the reduced imine nitrogen; optionally deprotecting; extracting and isolating the desired compound.

26. A process according to claim 25 wherein the reagent of step (a) is an isocyanate compound having the formula Aryl—N=C=O.

27. A process according to claim 25 wherein the reagent of step (a) is an amine compound having the formula Aryl—NH$_2$ in combination with carbonyldiimidazole.

28. A pharmaceutical composition for treating bacterial infections comprising a therapeutically effective amount of a compound of claim 1, or a pharmaceutically acceptable salt or ester thereof, in combination with a pharmaceutically acceptable carrier.

29. A method for treating bacterial infections comprising administering to a mammal in need of such treatment a pharmaceutical composition containing a therapeutically-effective amount of a compound of claim 1, or a pharmaceutically acceptable salt or ester thereof.

* * * * *